US010046057B2

(12) United States Patent
Tatro et al.

(10) Patent No.: US 10,046,057 B2
(45) Date of Patent: Aug. 14, 2018

(54) METHODS FOR ARRANGING AND PACKING NUCLEIC ACIDS FOR UNUSUAL RESISTANCE TO NUCLEASES AND TARGETED DELIVERY FOR GENE THERAPY

(71) Applicant: The Regents of the University of California, Oakland, CA (US)

(72) Inventors: Erick T. Tatro, San Diego, CA (US); Nathan Gianneschi, San Diego, CA (US); Anthony M. Rush, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/667,283

(22) Filed: Mar. 24, 2015

(65) Prior Publication Data
US 2015/0190525 A1    Jul. 9, 2015

Related U.S. Application Data

(63) Continuation of application No. PCT/US2013/061466, filed on Sep. 24, 2013.

(60) Provisional application No. 61/704,851, filed on Sep. 24, 2012.

(51) Int. Cl.
| | | |
|---|---|---|
| A61K 47/48 | (2006.01) |
| C12N 15/11 | (2006.01) |
| A61K 48/00 | (2006.01) |
| C12N 15/87 | (2006.01) |
| C12N 15/113 | (2010.01) |

(52) U.S. Cl.
CPC .... *A61K 47/48176* (2013.01); *A61K 48/0041* (2013.01); *C12N 15/11* (2013.01); *C12N 15/111* (2013.01); *C12N 15/113* (2013.01); *C12N 15/87* (2013.01); *C12N 2310/113* (2013.01); *C12N 2310/3231* (2013.01); *C12N 2310/351* (2013.01); *C12N 2310/353* (2013.01); *C12N 2310/3515* (2013.01); *C12N 2320/32* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 2004/0033345 A1 | 2/2004 | Dubertret et al. | |
| 2005/0136258 A1 | 6/2005 | Nie et al. | |
| 2009/0220418 A1 | 9/2009 | Pison et al. | |
| 2011/0158906 A1* | 6/2011 | Mullen | A61K 47/60 424/1.73 |

FOREIGN PATENT DOCUMENTS

| | | |
|---|---|---|
| WO | WO-01/87227 A2 | 11/2001 |
| WO | WO-01/87227 A3 | 11/2001 |
| WO | WO-2012/001012 A2 | 1/2012 |
| WO | WO-2012-001012 A3 | 1/2012 |

OTHER PUBLICATIONS

Kwak et al., Angew. Chem. Int. Ed. 2010, 49, 8574-8587.*
Reth, M., Nature Immunology, Aug. 2013, 14(8)765-767.*
Droumaguet et al., Polymer Chemistry, 2010, 1:563-598.*
Alemdaroglu, F.E. et al. (May 7, 2007, e-published Feb. 21, 2007). "DNA meets synthetic polymers--highly versatile hybrid materials," *Org Biomol Chem* 5(9):1311-1320.
Chien, M.P. et al. (Jul. 12, 2010). "Programmable shape-shifting micelles," *Angew Chem Int Ed Engl* 49(30):5076-5080.
International Search Report dated Dec. 24, 2013, for PCT Application No. PCT/US2013/061466, filed Sep. 24, 2013, 5 pages.
Written Opinion dated Dec. 24, 2013, for PCT Application No. PCT/US2013/061466, filed Sep. 24, 2013, 11 pages.

* cited by examiner

*Primary Examiner* — James D Schultz
(74) *Attorney, Agent, or Firm* — Mintz Levin Cohn Ferris Glovsky and Popeo, P.C.

(57) ABSTRACT

There are disclosed compositions and methods to render nucleic acids resistant to nuclease digestion while maintaining sequence selective hybridization competency. The approach relies on utilizing nucleic acids as the polar head group of a nucleic acid-polymer amphiphile in order to assemble well-defined, discrete micellar nanoparticles. Dense packing of nucleic acid in the micelle corona allows for hybridization of complementary oligonucleotides while prohibiting enzymatic degradation.

8 Claims, 20 Drawing Sheets

Particle 1 (P1) ssDNA-1 sequence:
5'-TTTAGAG-T$_F$-CATGTCCAGTCAG-T$_D$-G

Particle 2 (P2) ssDNA-2 sequence:
5'-TTTAGAG-T$_D$-CATGTCCAGTCAG-T$_F$-G

METHODS FOR ARRANGING AND PACKING NUCLEIC ACIDS FOR UNUSUAL RESISTANCE TO NUCLEASES AND TARGETED DELIVERY FOR GENE THERAPY

CROSS-REFERENCES TO RELATED APPLICATIONS

This application is a continuation of International Appl. No. PCT/US2013/061466, filed Sep. 24, 2013, which claims the benefit of U.S. Provisional Appl. No. 61/704,851, filed Sep. 24, 2012, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under grant numbers 1R03DA031591 and OD008724, awarded by the National Institutes of Health. The Government has certain rights in this invention.

REFERENCE TO A "SEQUENCE LISTING," A TABLE, OR A COMPUTER PROGRAM LISTING APPENDIX SUBMITTED AS AN ASCII FILE

The Sequence Listing written in file 48537-527C01US_ST25.TXT, created on Mar. 20, 2015, 14,405 bytes, machine format IBM-PC, MS-Windows operating system, is hereby incorporated by reference.

BACKGROUND OF THE INVENTION

Nucleic acids are unique, informational molecules with exceptional potential in the preparation of complex nanostructured materials with utility as potent and specific therapeutic agents in vivo and as powerful investigative tools in vitro. See e.g., Winfree, E. et al., 1998 *Nature* 394:539-544; Akhtar, S. et al., 2000, *Adv. Drug Deliv. Rev.* 44:3-21; Thomas, M. & Klibanov, A. M., 2003, *App. Microbiol. Biotechnol.* 62:27-34; Davis, M., 2002, *E. Curr. Opinion Biotechnol.* 13:128-131. Despite this promise, unmodified nucleic acids are inherently susceptible to enzymatic degradation in biological milieu, limiting their practical utility in detection and as therapeutics in real-world applications. To mitigate these issues, considerable effort has been applied to the generation of DNA analogues capable of resisting attack. See e.g., Leumann, C. J., 2002, *Bioorg. Med. Chem.* 10:841-854; Eschenmoser, A., 2005, *Chimia* 59:836-850. However, an optimal approach would preserve the natural nucleic acid sequence and associated hybridization properties. Therefore, new approaches for the preparation of well-defined, stable and competent nucleic acid-based materials are required.

BRIEF DESCRIPTION OF THE INVENTION

In a first aspect, there is provided a nucleic acid conjugate including a first oligonucleotide comprising up to about 200 bases, wherein the first oligonucleotide is complementary to a target sequence associated with aberrant physiological activity, and a hydrophobic polymer covalently bound to the first oligonucleotide through a first linker, wherein the conjugate forms nanoparticulate micelles having a hydrophobic core and a hydrophilic shell, wherein the hydrophobic core includes a plurality of hydrophobic polymer moieties, and wherein the hydrophilic shell includes a high density of said first oligonucleotide.

In another aspect, there is provided a targeted polymer nanoparticle including a plurality of nucleic acid conjugates as disclosed herein.

In another aspect, there is provided a micelle including a plurality of nucleic acid conjugates as disclosed herein.

In another aspect, there is provided a formulation including a nucleic acid conjugate as disclosed herein.

In another aspect, there is provided a method of making a nucleic acid conjugate as disclosed herein. The method includes reacting a first oligonucleotide comprising up to about 200 bases with a carboxylic acid terminated, hydrophobic polymer, optionally in the further presence of a first linker.

In another aspect, there is provided a method for delivery of an oligonucleotide into a target cell. The method includes administering an effective amount of a formulation as disclosed herein to a subject in need thereof.

In another aspect, there is provided a method to impart endonuclease resistance to a first oligonucleotide, wherein the first oligonucleotide has a defined sequence. The method includes incorporating the first oligonucleotide into a nucleic acid conjugate as disclosed herein, and forming a micelle therefrom prior to exposure of the first oligonucleotide to an endonuclease.

BRIEF DESCRIPTION OF THE DRAWINGS

FIG. 1A: Scheme for preparation of DNA-polymer amphiphiles (DPAs) and assembly of micelles. Synthesis: i) A hydrophobic polymer, terminally modified with a carboxylic acid moiety was mixed with a coupling agent and reacted with a 5'-amino modified oligonucleotide on solid support (controlled pore glass, CPG). ii) The resulting DNA-polymer conjugate is deprotected and cleaved from solid support. iii) Dialysis of cleaved DPA into deionized water affords a mixture of micelles and free, unreacted nucleic acid. Sequence legend: (Particle 1, P1) TTTAGAGT$_F$CATGTCCAGTCAGT$_D$G (SEQ ID NO:2); (Particle 2, P2) TTTAGAGT$_D$CATGTCCAGTCAGT$_F$G (SEQ ID NO:3); (Non-labeled DNA) TTTAGAGTCATGTCCAGTCAGTG (SEQ ID NO:1). FIG. 1B: PAGE analysis. Lane 1 (left): Crude material post-micelle (P1) formation showing conjugate (top band) and free ssDNA (lower band). Lane 2 (middle): HPLC purified sample of ssDNA-1. Lane 3 (right): Purified P1, isolated via size-exclusion chromatography (SEC). FIG. 1C: SEC trace of purified P1 ($\lambda_{abs}$=260 nm). FIG. 1D): Transmission electron micrograph of P1. See Examples for P2 data and all detailed reaction conditions, reagents and purification techniques.

FIG. 2A depicts Nt.CviPII activity over time (min) monitored via fluorescein fluorescence dequenching ($\lambda_{ex}$=485 nm, $\lambda_{em}$=535 nm). Legend: ssDNA-1 (diamond); P1 (circle); ssDNA-2 (box); P2 (triangle). FIG. 2B depicts thermal denaturation analysis with and without Nt.CviPII treatment for P1 and ssDNA-1 ($\lambda_{abs}$=260 nm). Samples were subjected to enzyme for 100 minutes at 37° C. Results: ssDNA-1+Complement: Tm=63.9° C.; ssDNA-1+Nt.CviPII+Complement: Tm=37.8° C.; P1+Complement: T$_m$=58.8° C.; P1+Nt.CviPII+Complement: T$_m$=58.3° C.). Symbol legend: ssDNA-1 (line ending at top); ssDNA-1+nick (diamond); P1 (line below top line); P1+nick (circle). Complement sequence: TATTATATCTTTAGAC ACTGACTGGACATGACTCT (SEQ ID NO:4). FIG. 2C depicts thermal denaturation analysis with and without Nt.CviPII treatment for P2 and ssDNA-2 ($\lambda_{abs}$=260 nm). Samples were subjected to enzyme for 100 minutes at 37° C. Results: ssDNA-2+Complement: Tm=63.9° C.; ssDNA-2+Nt.CviPII+Complement: Tm=37.8° C.; P2+Complement: $T_m$=56.9° C.; P2+Nt.CviPII+Complement: $T_m$=55.3° C.). Symbol legend: ssDNA-2 (lower line); ssDNA-2+nick (box); P2 (upper line); P2+nick (triangle). See Examples for experimental details.

FIG. 3A depicts Exonuclease III (ExoIII) activity over time (min) monitored by fluorescein fluorescence de-quenching ($\lambda_{ex}$=485 nm, $\lambda_{em}$=535 nm). Legend: ssDNA-1 (diamond); P1 (circle); ssDNA-2 (box); P2 (triangle). FIG. 3B depicts thermal denaturation analysis with and without ExoIII treatment for P1 and ssDNA-1 ($\lambda_{abs}$=260 nm). Samples were subjected to enzyme for 60 minutes at 37° C. Legend: ssDNA-1 (line ending at top); ssDNA-1+ExoIII (diamond); P1 (line below top line); P1+ExoIII (circle). Complement sequence (see FIG. 2B). Results: P1+Complement: $T_m$=58.8° C.; P1+ExoIII+Complement: $T_m$=55.8° C.). FIG. 3C depicts thermal denaturation analysis with and without ExoIII treatment for P2 and ssDNA-2 ($\lambda_{abs}$=260 nm). Samples were subjected to enzyme for 60 minutes at 37° C. Legend: ssDNA-2 (lower line); ssDNA-2+ExoIII (box); P2 (upper line); P2+ExoIII (triangle). Complement sequence (see FIG. 2B). Results: P2+Complement: $T_m$=56.9° C.; P2+ExoIII+Complement: $T_m$=53.9° C.). See Examples for experimental details.

FIG. 8A depicts HPLC chromatogram of purified ssDNA-1 ($\lambda_{abs}$=290 nm, gradient: 36-60% B in 50 minutes). FIG. 8B depicts HPLC chromatogram of purified ssDNA-2 ($\lambda_{abs}$=290 nm, gradient: 36-60% B in 50 minutes). FIG. 8C depicts MALDI-TOF mass spectrum of ssDNA-1: m/z=obs: 8295.45; theo: 8292.07. Calibration was performed externally. FIG. 8D depicts MALDI-TOF mass spectrum of ssDNA-2: m/z=obs: 8295.36; theo: 8292.07. Calibration was performed internally (left-to-right): std. m/z=obs: 3646.21; theo: 3646.4, obs: 6118.48; theo: 6118.0, obs: 9191.64; theo: 9192.0.

FIG. 10A: DLS histogram for P1 showing aggregates with a hydrodynamic diameter of 20 nm (10 mM Tris pH 8.5, 25° C., mass weighted intensity signal). FIG. 10B: DLS histogram for P2 showing aggregates with a hydrodynamic diameter of 20 nm (10 mM Tris pH 8.5, 25° C., mass weighted intensity signal). FIG. 10C: SLS/DLS analysis of P1 versus BSA protein standard, $M_w$=4,000,000 g/mol, $N_{agg}$=295 DPA/nanoparticle (DPA $M_w$=5221 g/mol (polymer)+8295 g/mol (oligo)=13516 g/mol; 4,000,000/13516=295, 295/(4*3.14*($10^2$))=0.23 DNA/$nm^2$). Legend: Light scattering (darker line on top at right); Counter rate (lighter line below at right). FIG. 10D: DLS histogram of P1 in ExoIII reaction buffer at 37° C. showing stability against aggregation. Potassium acetate was added in order to prevent aggregation due to $MgCl_2$ in NE Buffer 1. FIG. 10E: DLS histogram of P1 in Nt.CviPII reaction buffer at 37° C. showing stability against aggregation.

FIG. 12A: ExoIII activity, shown as fluorescence de-quenching over time for ssDNA-2 and P2, plotted as concentration of liberated fluorescein dT. Legend: ssDNA-2 (box); P2 (circle). FIG. 12B: Initial rate data for ExoIII vs. ssDNA-2 at varying concentrations of ssDNA-2. Legend: ssDNA-2 at 1 µM (circle); 2 µM (triangle tip up); 5 µM (triangle tip down); 10 µM (diamond). FIG. 12C: Initial rate data for ExoIII vs. P2 at varying concentrations of P2. Legend: P2 at 1 µM (box); 2 µM (circle); 5 µM (triangle). FIG. 12D: Lineweaver-Burk plot for ExoIII activity on ssDNA-2. FIG. 12E: Lineweaver-Burk plot for ExoIII activity on P2. FIG. 12F: Fluorescein dT fluorescence calibration curve showing a linear increase in fluorescence with increasing concentration of the free phosphoramidite (upper line). Shown in lower line is an analogous calibration curve for a DPA-nanoparticle identical to P1 but not containing a DABCYL quencher moiety. The drastic difference in slopes for the two fluorescent systems is indicative of the unique environment of the fluorescein molecule on the nanoparticle. Legend: Fluorescein particle (box); Fluorescein dT (circle). FIG. 12G: Bradford assay calibration curve constructed using BSA standard and dye reagent (Bio-Rad #500-0002). ExoIII sample is plotted at circle, indicating a concentration of 55 µg/mL.

FIG. 13A: ssDNA-1 and P1. FIG. 13B: ssDNA-2 and P2. For substrate+ExoIII, the experiment was conducted as described herein. For substrate control melting curves, the substrate (ssDNA or DPA-nanoparticle) was treated in an identical fashion except no enzyme or complementary DNA was added before conducting melting temperature analysis. Furthermore, complementary DNA on its own was analyzed in a similar fashion (i.e., no ssDNA, particle, or enzyme present). The absorbance spectra for this complement on its own was added to that of the control ssDNA or DPA nanoparticle to produce the control spectrum (solid lines without symbols) in the above figures. This comparison highlights the fact that ssDNA, after digestion with ExoIII, is unable to form a significant duplex with its complement. Therefore, ssDNA-1 (FIG.

13A) and ssDNA-2 (FIG. 13B) exhibit featureless melting curves identical to the sum of the absorbance curves for both ssDNA strands on their own. Legend (FIG. 13A): ssDNA-1 ctrl (lower line at right); ssDNA-1+ExoIII (diamond); P1 ctrl (upper line at right); P1+ExoIII (circle); (FIG. 13B): ssDNA-2 ctrl (upper line at right); ssDNA-2+ExoIII (box); P2 ctrl (lower line at right); P2+ExoIII (triangle).

DETAILED DESCRIPTION OF THE INVENTION

I. Definitions

Figure 1A:
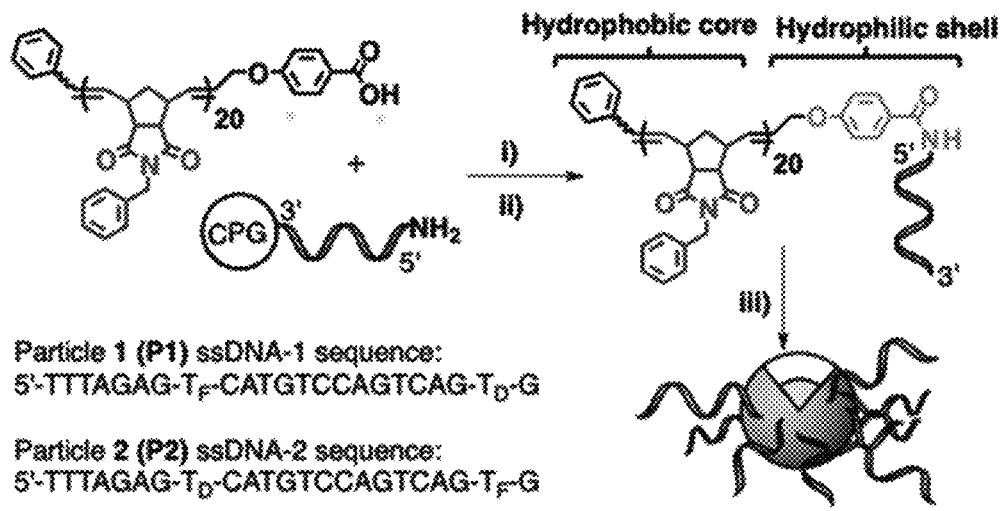
FIGS. 1A-1D.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, butadienyl, 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

The term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g., from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, and —NO$_2$ in a number ranging from zero to (2 m'+1), where m' is the total number of carbon atoms in such radical. R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula (CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
  (A) —OH, —NH$_2$, —SH, —CN, —CF$_3$, —CCl$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and
  (B) alkyl, heteroalkyl, cycloalkyl, heterocycloalkyl, aryl, and heteroaryl, substituted with at least one substituent selected from:
    (i) oxo, —OH, —NH$_2$, —SH, —CN, —CF$_3$, —CCl$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (ii) alkyl, heteroalkyl, cycloalkyl, heterocycloalkyl, aryl, and heteroaryl, substituted with at least one substituent selected from:
      (a) oxo, —OH, —NH$_2$, —SH, —CN, —CF$_3$, —CCl$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
      (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —CCl$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In some embodiments, a compound described herein can include multiple instances of a substituent. In such embodiments, each substituent may optional be different at each occurrence and be appropriately labeled to distinguish each group for greater clarity. Unless indicated otherwise, it is understood that each instance of a particular substitution is independent of other substitutions in a compound disclosed herein.

The terms "linker" and the like as used herein mean a divalent or trivalent species covalently bonding two or three linked moieties, respectively. Accordingly, the terms "linked moiety" and the like refer to the chemical linking of chemical moieties through a linker. In one embodiment, the linker is a divalent linker. In one embodiment, the linker is a trivalent linker. In one embodiment, the linker is a bond. In one embodiment, the linker has a free amine group available for covalent bonding to a linked moiety. In one embodiment, the linker forms an amide bond to a linked moiety. In one embodiment, the linker has a free carboxyl group available for covalent bonding to a linked moiety. In one embodiment, linkage is through a phosphoester bond, as known in the art. In one embodiment, linkage to a nucleic acid compound is through a phosphoester bond. In embodiments, the linker further includes a spacer element. Exemplary spacer elements include alkylene, polyethylene glycol (PEG), and the like, as known in the art.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, detection of an infectious pathogen, neuropsychiatric exams, and/or a psychiatric evaluation. A candidate molecule or compound described herein may be in an amount in a formulation or medicament, which is an amount that can lead to a biological effect, or lead to ameliorating, alleviating, lessening, relieving, diminishing or removing symptoms of a condition, e.g., disease, for example. The terms also can refer to reducing or stopping a cell proliferation rate (e.g., slowing or halting tumor growth) or reducing the number of proliferating cancer cells (e.g., removing part or all of a tumor). These terms also are applicable to reducing a titer of a microorganism (microbe) in a system (e.g., cell, tissue, or subject) infected with a microbe, reducing the rate of microbial propagation, reducing the number of symptoms or an effect of a symptom associated with the microbial infection, and/or removing detectable amounts of the microbe from the system. Examples of microbe include but are not limited to virus, bacterium and fungus.

The terms "subject," "patient" or "subject in need thereof" refers to a living organism suffering from or prone to a disease or condition that can be treated by administration of a compound, pharmaceutical composition, mixture or vaccine as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a domesticated animal. In some embodiments, a patient is a dog. In some embodiments, a patient is a parrot. In some embodiments, a patient is a livestock animal. In some embodiments, a patient is a mammal. In some embodiments, a patient is a cat. In some embodiments, a patient is a horse. In some embodiments, a patient is bovine. In some embodiments, a patient is a canine. In some embodiments, a patient is a feline. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a hamster. In some embodiments, a patient is a test animal. In some embodiments, a patient is a newborn animal. In some embodiments, a patient is a newborn human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

The term "effective amount" as used herein refers to an amount effective to achieve an intended purpose. Accordingly, the terms "therapeutically effective amount" and the like refer to an amount of a compound, mixture or vaccine, or an amount of a combination thereof, to treat or prevent a disease or disorder, or to treat a symptom of the disease or disorder, in a subject in need thereof.

The term "polymer" refers, in the usual and customary sense, to a macromolecule having repeating units connected by covalent bonds. Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically block copolymers of a hydrophilic segment and a hydrophobic segment. Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

The term "nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which can have similar binding properties as the reference nucleic acid, and which can be metabolized in a manner similar to the reference nucleotides (i.e., "modified nucleotides"). Examples of such analogs include, without limitation, phosphorothioates, phosphoramidates, methyl phosphonates, chiral-methyl phosphonates, 2-O-methyl ribonucleotides, and the like. The term further encompasses "locked nucleic acids (LNAs)," as known in the art, which contain an extra bridging connecting the 2' oxygen and 4' carbon of the ribose moiety. See e.g., Kaur, H., et al., *Biochemistry* 2006, 45:7347-7355. The terms "nucleotide" and "base" refer to ribonucleotides or deoxyribonucleotides, including analogs or modified backbone residues or linkages thereof as disclosed herein. The word "polynucleotide" refers to a linear sequence of nucleotides. The nucleotides can be ribonucleotides, deoxyribonucleotides, or a mixture of both, including nucleotide analogs or modified backbone residues or linkages as disclosed herein. Examples of polynucleotides contemplated herein include single and double stranded DNA, single and double stranded RNA (including micro-RNA [miRNA] as known in the art), and hybrid molecules having mixtures of single and double stranded DNA, RNA, or LNA. Accordingly, the polynucleotides described herein may contain one or more modified nucleotides as disclosed herein. The term "oligonucleotide" refers to a polynucleotide, as disclosed herein, generally having a number of bases not greater than about 200.

The term "antisense," "siRNA," or "RNAi" refers to a nucleic acid that forms a double stranded nucleic acid, which double stranded nucleic acid has the ability to reduce or inhibit expression of a target gene when expressed or inserted in the same cell as the target gene. The complementary portions of the nucleic acid that hybridize to form the double stranded molecule typically have substantial or complete identity. In one embodiment, an antisense nucleic acid, siRNA or RNAi refers to a nucleic acid that has substantial or complete identity to a target gene and forms a double stranded siRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length. In embodiments, the length is 10-30 base nucleotide, e.g., 10, 11, 12, 13, 14, 15, 16, 17, 18, 19, 20, 21, 22, 23, 24, 25, 26, 27, 28, 29 or 30 nucleotides in length.

The terms "complementary," "complementarity" and the like refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing. The terms "at least partially complementary" and the like refer to two or more polynucleotides having at least a specified non-zero percent identity, e.g., at least 10%, 20%, 30%, 40%, 50%, 60%, 70%, 80%, 90%, or even greater percent identity.

The terms "identical" or "percent identity" in the context of two or more polynucleotides refers to two or more sequences or subsequences that are the same or have a specified percentage of nucleotides that are the same (i.e., about 60%, 65%, 70%, 75%, 80%, 85%, 90%, 91%, 92%, 93%, 94%, 95%, 96%, 97%, 98%, 99%, or higher identity over a specified region) when compared and aligned for maximum correspondence over a comparison window or designated region, respectively, as measured using a BLAST or BLAST 2.0 sequence comparison algorithm as known in the art, or by manual alignment and visual inspection. See, e.g., NCBI web site at www.ncbi.nlm.nih.gov/BLAST, or the like. Sequences having high percent identity (e.g., greater than 50%, 60%, 70%, 80%, 90% or even greater) are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 10-25, 10-50, 10-75, 10-100, 10-150, or even 10-200 nucleotides in length.

The term "catalytic chain transfer" refers, in the usual and customary sense, to a process of radical polymerization as known in the art which results in enhanced control of the resulting products, typically resulting in reduced polymeric chain size. See e.g., Enikolopyan, N. S., et al., *Polym. Sci., Part A: Polym. Chem.*, 1981, 19:879-889.

The terms "iniferter mediated polymerization" and the like refer, in the usual and customary sense, to polymerization employing an "iniferter" which, as known in the art, is a chemical compound that simultaneously acts as initiator, transfer agent, and terminator in controlled free radical polymerization reactions, e.g., dithiocarbamates. See e.g., Otsu, T., & Yashida, M., *Mackromol. Chem., Rapid Commun.*, 1982, 3:127-132.

The terms "stable free radical mediated polymerization,' "SRFP" and the like refer, in the usual and customary sense, to polymerization reactions wherein the coupling of the stable free radical with the polymeric radical is sufficiently reversible that the termination step is reversible, and the propagating radical concentration can be limited to levels that allow for controlled polymerization. See e.g., Veregin, R. P. N., et al., *Macromolecules* 1993, 26:5316-5320.

The terms "atom transfer radical polymerization," "ATRP" and the like refer, in the usual and customary sense, to methods of polymerization employing a transition metal catalyst, wherein the atom transfer step is the key step in the reaction responsible for uniform polymer chain growth. See e.g., Kato, M., et al., *Macromolecules* 1995, 28:1721-1723; Wang, J. & Matyjaszewski, K., *J. Am. Chem. Soc.* 1995, 117:5614-5615.

The terms "reversible addition fragmentation chain transfer polymerization," "RAFT" and the like refer, in the usual and customary sense, to methods of polymerization which use a chain transfer agent in the form of a thiocarbonylthio compound or the like to afford control over the generated molecular weight and polydispersity during a free-radical polymerization. See e.g., Yeole, N., *Synlett.* 2010(10): 1572-1573; Moad, G., et al., *Aust. J. Chem.*, 2005, 58:379-410.

The terms "iodine transfer polymerization," "ITP" and the like refer, in the usual and customary sense, to methods of polymerization known in the art which employ iodine to selectively moderate rates during propagation. See e.g., U.S. Pat. No. 4,243,770.

The term "ring opening metathesis polymerization," "ROMP" and the like refer, in the usual and customary sense, to types of olefin metathesis chain growth polymerization. See e.g., Grubbs, R. H. & Tumas, W., *Science* 1989, 243:907-915; Herisson, J. L. & Chauvin, Y., *Die Makromolekulare Chemie*, 1971, 141:161-176.

The term "micelle" means, in the usual and customary sense, an aggregate of amphipathic molecules in an aqueous milieu, with interior nonpolar portions and exterior polar portions. Amphiphilic molecules are known to form micelles above a particular concentration (i.e., the critical micellar concentration, CMC). The terms "nanoparticulate micelle," "micellar nanoparticle," "polymeric micelle" and the like refer to amphiphilic compounds, typically having a large solubility difference between hydrophilic and hydrophobic elements, which compounds are known to assemble in an aqueous milieu into micelles with a mesoscopic size range. For example, typical sizes for nanoparticulate micelles are in the range of about 10-500, 10-400, 10-300, 10-200, 1-100, 10-50, 10-40, 10-30, 10-20, 5-20 nm. It is known that such micelles have a fairly narrow size distribution and are characterized by a core-shell architecture (i.e., so-called "core-shell nanoparticles"), where hydrophobic segments are segregated from the aqueous exterior to form an inner core (i.e., "hydrophobic core") surrounded by a hydrophilic segment (i.e., "hydrophilic shell" or "corona").

The terms "cell specific targeting moiety" and the like refer to compounds which can be recognized and, optionally, taken up by a specific cell type. Such compounds can have sufficient chemical similarity to naturally occurring ligands to allow specific recognition by a receptor on the targeted cell. Exemplary cell specific target moieties include peptides, proteins including antibodies, polynucleotides, aptamers, and small molecule analogs of naturally occurring ligands. The manner of update can be specific receptor mediated uptake, endocytosis, and the like, as known in the art. See e.g., Prapainop, K., et al., *J. Am. Chem. Soc.* 2012, 134:4100-4103. Exemplary cell specific targeting moieties include β-CFT (methyl (1R,2S,3S,5S)-3-(4-fluorophenyl)-8-methyl-8-azabicyclo[3.2.1]octane-2-carboxylate) and analogs thereof, e.g., analogs suitable for bonding to a nucleic acid conjugate as disclosed herein.

The terms "target sequence associated with aberrant physiological activity" and the like as used herein refer to physiologic nucleic acid sequences (e.g., DNA or RNA) associated with a disease or disorder. Thus, by modulating the activity of the associated nucleic acid sequence, the severity of the disease or disorder can be attenuated. Diseases and disorders which contain target sequences associated with aberrant physiological activity include: cancer, a proliferative disease or disorder; apoptosis, a disease or disorder associated with impaired apoptosis regulation, diabetes, a cardiovascular disease or disorder, a lysosomal storage disorder, an inflammatory disease or disorder (e.g., inflammatory bowel disease, including Crohn's disease, ulcerative colitis, psoriasis, arthritis etc.), inflammation; a metabolic disease or disorder, metabolic syndrome, insulin resistance syndrome, diabetes, hyperlipidemia, fatty liver disease, cachexia, obesity, atherosclerosis, arterioscerlosis, a disease disorder or condition associated with altered cholesterol metabolism, elevated blood pressure, a neurological disease or disorder; a disease or disorder associated with impaired neuronal cell differentiation; a disease or disorder associated with impaired neurite formation; a disease or disorder associated with impaired glycoprotein desialylation and an infection (e.g., viral infection, systemic infection or any other type of infection). Exemplary named diseases or disorders which contain target sequences associated with aberrant physiological activity include: HIV infection (e.g., in AIDS), Parkinson's disease, Alzheimer's disease, amyotrophic lateral sclerosis, arthritis, cystic fibrosis, hemophilia, Tay Sachs disease, disease), addiction, and mood disorder. Neurological diseases and disorders that are amenable to treatment by methods disclosed herein can involve at least one of the following neurological tissues: hypothalamus, amygdala, pituitary, nervous system, brainstem, cerebellum, cortex, frontal cortex, hippocampus, striatum, and thalamus or other regions of the central or peripheral nervous system.

The terms "detectable label" and the like refer, in the usual and customary sense, to a chemical moiety that affords detectability to a species attached therewith. Exemplary detectable labels include fluorescent label, luminescent label, radioactive label, spectroscopic label, stable isotope mass tagged label, electron spin resonance label, nuclear magnetic resonance label and chelated metal label, as known in the art.

The term "about" in the context of a numerical value refers, unless expressly indicated otherwise, to the nominal value ±10% thereof.

II. Compounds

In a first aspect, there is provided a nucleic acid conjugate including a first oligonucleotide which includes up to about 200 bases, wherein the first oligonucleotide is complementary to a target sequence associated with aberrant physiological activity, and a hydrophobic polymer covalently bound to the first oligonucleotide through a first linker, wherein the conjugate forms nanoparticulate micelles having a hydrophobic core and a hydrophilic shell, wherein the hydrophobic core includes a plurality of hydrophobic polymer moieties, and wherein the hydrophilic shell includes a high density of said first oligonucleotide.

Accordingly, in one embodiment the nucleic acid conjugate has structure S1 following:

"hydrophobic polymer"-$L_1$-"first oligonucleotide"  (S1), wherein first linker "$L_1$" is a divalent linker as disclosed herein. In one embodiment, linker $L_1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In one embodiment, bonding of linker $L_1$ to the hydrophobic polymer and/or the first oligonucleotide is through a substituent of a substituted cycloalkylene, substituted heterocycloalkylene, substituted arylene, or substituted heteroarylene. In one embodiment, linker $L_1$ includes a carboxyl-substituted cycloalkylene. In one embodiment, linker $L_1$ includes a carboxyl-substituted arylene. In one embodiment, linker $L_1$ includes an O-alkyl carboxyl-substituted arylene. In one embodiment, linker $L_1$ forms a amide bond with the first oligonucleotide.

In one embodiment, the first oligonucleotide includes a number of bases in the range of about 10-200, 10-180, 10-160, 10-140, 10-120, 10-100, 10-80, 10-60, 10-40, 10-30, 10-28, 10-26, 10-24, 10-22, 10-20, 10-18, 10-16, 10-14, or 10-12. In one embodiment, the number of bases is about 200, about 180, about 160, about 140, about 120, about 100, about 80, about 60, about 40, about 30, about 20, or about 10. In one embodiment, the number based in the first oligonucleotide is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

The first oligonucleotide is complementary to a target sequence, e.g., a physiologic target sequence, which is associated with aberrant physiological activity, as disclosed herein. In one embodiment, the complementarity is absolute. In one embodiment, the complementarity is partial. In one embodiment, the first oligonucleotide is at least partially complementary to a target sequence, e.g., 50%, 60%, 70%, 80%, 90%, 92%, 94%, 96%, 98% or greater percentage identity to the target sequence.

In one embodiment, the first oligonucleotide is a DNA, an RNA, or a locked nucleic acid (LNA). In one embodiment, the first oligonucleotide contains DNA, RNA or LNA bases. In one embodiment, the first oligonucleotide contains a combination of at least two of DNA, RNA and LNA bases. In one embodiment, the first oligonucleotide contains DNA, RNA and LNA bases.

The nucleic acid conjugate forms a nanoparticulate micelle having a hydrophobic core and a hydrophilic shell. The hydrophobic core includes a plurality of hydrophobic polymer moieties, as disclosed herein. The hydrophilic shell includes a high density of the first oligonucleotide. The terms "high density of the first oligonucleotide" and the like refer to a density of nucleic acid on the order of 0.05 to 0.5 strands/$nm^2$ on the surface of the nanoparticulate micelle. In one embodiment, the density of the first oligonucleotide on the surface of the nanoparticulate micelle is about 0.05, 0.1, 0.12, 0.14, 0.16, 0.18, 0.2, 0.22, 0.24, 0.36, 0.28, 0.3, or even 0.4 strands/$nm^2$. In one embodiment, the density is about 0.2 strands/$nm^2$. In one embodiment, the micellar nanoparticle has about 20-400 oligonucleotides per micellar nanoparticle, e.g., about 20-400, 20-380, 20-360, 20-340, 20-320, 20-300, 20-280, 20-260, 20-240, 20-220, 20-200, 20-180, 20-160, 20-140, 20-120, 20-100, 20-80, 20-60, or 20-40. In one embodiment, the micellar nanoparticle has about 200 oligonucleotides per micellar nanoparticle.

In one embodiment, the hydrophobic polymer linked to the first oligonucleotide is a hydrophobic homopolymer. In one embodiment, the hydrophobic homopolymer is an alkyl chain.

In one embodiment, the hydrophobic polymer is a hydrophobic block copolymer or a hydrophobic homopolymer. In one embodiment, the hydrophobic polymer is a hydrophobic block copolymer. In one embodiment, the hydrophobic polymer is a hydrophobic homopolymer. In one embodiment, the hydrophobic polymer includes a polymerization product of (N-Benzyl)-5-norbornene-exo-2,3-dicarboximide.

In one embodiment, the hydrophobic polymer is selected from polymers made by catalytic chain transfer, iniferter mediated polymerization, stable free radical mediated polymerization (SFRP), atom transfer radical polymerization (ATRP), reversible addition fragmentation chain transfer polymerization (RAFT), iodine-transfer polymerization, or ring opening metathesis polymerization (ROMP). In one embodiment, the hydrophobic polymer is prepared by the use of ROMP methods.

In one embodiment, the hydrophobic polymer is covalently linked, directly or indirectly, to the first oligonucleotide via an amide bond. The term "directly linked" in this context means that linker $L_1$ contains an amide bond which directly bonds to either the hydrophobic polymer or the first oligonucleotide. The term "indirectly linked" in this context means that linker $L_1$ contains an amide bond, which amide bond does not directly bond to the hydrophobic polymer or the first oligonucleotide.

In one embodiment, the nucleic acid conjugate further includes a first cell specific targeting moiety as disclosed herein covalently linked to the first linker. Accordingly, in this embodiment, the nucleic acid conjugate has structure S2 following:

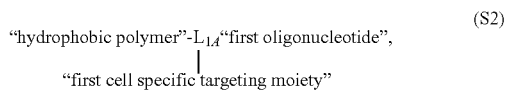

(S2)

wherein first linker "$L_{1A}$" is a trivalent linker as disclosed herein. In one embodiment, linker $L_{1A}$ contains substituted alkylene, substituted heteroalkylene, substituted cycloalkylene, substituted heterocycloalkylene, substituted arylene, or substituted heteroarylene, wherein at least one of the bonds to the hydrophobic polymer, first oligonucleotide or first cell specific targeting moiety is through a substituent of first linker "$L_{1A}$."

In one embodiment, the nucleic acid conjugate further includes a first cell specific targeting moiety as disclosed herein covalently linked to the first oligonucleotide, optionally through a second linker. Accordingly, in this embodiment, the nucleic acid conjugate has structure S3 following:

"hydrophobic polymer"-$L_1$-"first oligonucleotide"-
$L_2$-"first cell specific targeting moiety"    (S3), wherein first linker "$L_1$" is as disclosed above, and second linker "$L_2$," if present, is a divalent linker with structure of linker "$L_1$."

Further to the nucleic acid conjugate having structure S3, in one embodiment the nucleic acid conjugate further includes a second cell specific targeting moiety covalently bound to the hydrophobic polymer, having structure S4 following:

wherein first linker "$L_1$" and second linker "$L_2$" are as disclosed above, and third linker "$L_3$," if present, is a divalent linker with structure of linker "$L_1$." The second cell specific targeting moiety can be the same or different than the first cell specific targeting moiety. In one embodiment, the second cell specific targeting moiety is different than the first cell specific targeting moiety. In one embodiment, the second cell specific targeting moiety is the same as the first cell specific targeting moiety.

Further to any embodiment with structure S1, in one embodiment the nucleic acid conjugate further includes a first cell specific targeting moiety covalently bound to the hydrophobic polymer, optionally through a fourth linker "L4" and having the structure S5 following:

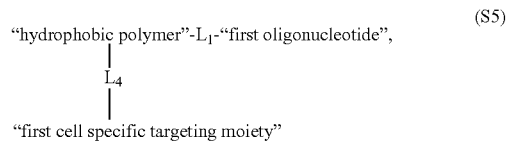

(S5)

wherein fourth linker "$L_4$," if present, is a divalent linker with structure of linker "$L_1$" which links the hydrophobic polymer with the first cell specific targeting moiety.

Further to any embodiment of the nucleic acid conjugate having structure S1, in one embodiment the nucleic acid conjugate further includes a second oligonucleotide which is at least partially complementary to the first oligonucleotide. In one embodiment, the second oligonucleotide is hybridized to the first oligonucleotide. In one embodiment, the nucleic acid further includes a detectable label as described herein.

Further to any embodiment of the nucleic acid conjugate which includes a second oligonucleotide which is at least partially complementary to the first oligonucleotide and is hybridized thereto, in one embodiment the nucleic acid conjugate has structure S6 following:

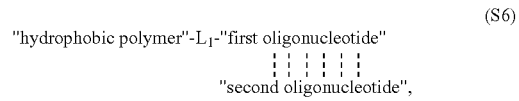

(S6)

wherein the dotted lines in S6 represent hybridization, as known in the art, of the first oligonucleotide with the second oligonucleotide. Further to this embodiment, in one embodiment the nucleic acid conjugate further includes a detectable label, as described herein.

Further to any embodiment of the nucleic acid conjugate which includes a second oligonucleotide which is at least partially complementary to the first oligonucleotide, in one embodiment the nucleic acid conjugate has structure S7 following:

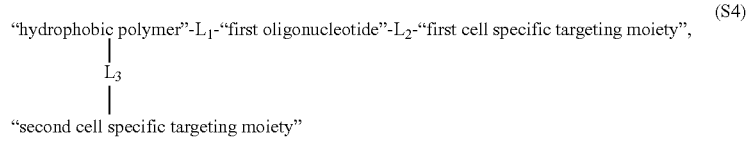

(S4)

(S7)

```
"hydrophobic polymer"-L₁-"first oligonucleotide"
                      ┊ ┊ ┊ ┊ ┊
             "second oligonucleotide"-L₅-"first cell specific targeting moiety",
``` wherein fifth linker "L₅," if present, is a divalent linker with structure of linker "L₁," and the dotted lines in S7 represents hybridization of the first oligonucleotide with the second oligonucleotide. Further to this embodiment, in one embodiment the nucleic acid conjugate further includes a detectable label, as described herein.

Further to any embodiment disclosed herein wherein the nucleic acid conjugate includes a first oligonucleotide, in one embodiment the nucleic acid conjugate includes a plurality of first oligonucleotides, each first oligonucleotide being independent of every other first oligonucleotide.

III. Targeted Polymer Nanoparticles

In another aspect, there is provided a targeted polymer nanoparticle including a plurality of nucleic acid conjugates as disclosed herein having structure S2, S3, S4, or S5, as disclosed herein.

In one embodiment, the nucleic acid conjugate has structure S2. In one embodiment, the nucleic acid conjugate has structure S3. In one embodiment, the nucleic acid conjugate has structure S4. In one embodiment, the nucleic acid conjugate has structure S5. In one embodiment, the targeted polymer nanoparticle includes nucleic acid conjugates with structure of at least two of S2, S3, S4, or S5. In one embodiment, the targeted polymer nanoparticle includes a plurality of nucleic acid conjugates as disclosed herein having structure S2, S3, S4, S5, or S7.

In another aspect, there is provided a targeted polymer nanoparticle including a plurality of nucleic acid conjugates as disclosed herein having structure S7. In one embodiment, the targeted polymer nanoparticle includes a plurality of nucleic acid conjugates as disclosed herein having structure S7 and any one of structures S2, S3, S4, or S5.

IV. Micelles

In another aspect, there is provided a micelle including a plurality of nucleic acid conjugates as disclosed herein with structure of S1, S2, S3, S4, S5, or S6.

In one embodiment, the micelle further includes a second oligonucleotide which is at least partially complementary to the first oligonucleotide, wherein the second oligonucleotide includes a first cell specific targeting moiety covalently attached thereto. In one embodiment, the micelle further includes a second oligonucleotide which is at least partially complementary to the first oligonucleotide, wherein the second oligonucleotide includes a first cell specific targeting moiety covalently attached thereto, and wherein the second oligonucleotide is hybridized to the first oligonucleotide.

In one embodiment, the micelle further includes a detectable label covalently attached to the first oligonucleotide. In one embodiment, the micelle further includes a detectable label covalently attached to the second oligonucleotide. In one embodiment, the micelle further includes a detectable label covalently attached to the first oligonucleotide and the second oligonucleotide.

V. Pharmaceutical Compositions

In another aspect, there is provided a pharmaceutical composition including a nucleic acid conjugate with structure S1, S2, S3, S4, S5, or S6 in a pharmaceutically acceptable carrier therefore. In another aspect, there is provided a pharmaceutical composition including a nucleic acid conjugate with structure S7 in a pharmaceutically acceptable carrier therefore.

The terms "pharmaceutically acceptable" and the like refer, in the usual and customary sense, to a compound or composition which can be administered to a subject without causing a significant adverse toxicological effect, as judged by a medical or veterinary professional.

Accordingly, the terms "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The pharmaceutical compositions include optical isomers, diastereomers, or pharmaceutically acceptable salts of the compounds disclosed herein. For example, in some embodiments, the pharmaceutical compositions include a compound of the present invention and citrate as a pharmaceutically acceptable salt. The compounds included in the pharmaceutical composition may be covalently attached to a carrier moiety. Alternatively, the compound included in the pharmaceutical composition is not covalently linked to a carrier moiety.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

A. Formulations

The compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention, i.e., "pharmaceutical formulation."

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds disclosed herein are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. A formulation for intravenous infusion could have a volume (e.g., 250-1000 mL) of fluid (e.g., sterile Ringer's solution, physiological saline, dextrose solution, Hank's solution and the like) and a therapeutically effective amount of a compound disclosed herein. Dose may vary depending on the type and severity of the disease. Dosages for any one subject depends upon many factors, including the body size, body surface area, age, the particular compound to be administered, sex, time and route of administration, general health, and other drugs being administered concurrently. Progress may be monitored by periodic assessment. For repeated administrations over several days or longer, depending on the condition, the treatment can be repeated until a desired suppression of disease symptoms occurs. The desired dosage can be delivered by a single bolus administration, by multiple bolus administrations, or by continuous infusion administration of compound. The compounds of the invention can also be incorporated into liposomes or administered via transdermal pumps or patches. Pharmaceutical admixtures suitable for use in the present invention include those described, for example, in PHARMACEUTICAL SCIENCES (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.01 mg to 1000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions provided by the present invention include compositions wherein the active ingredient is contained in a therapeutically effective amount. The actual amount effective for a particular application will depend, inter alia, on the condition being treated. For example, when administered in methods to treat cancer, such compositions will contain an amount of active ingredient effective to achieve the desired result (e.g., decreasing the number of cancer cells in a subject). For example, when administered to treat an infection, such compositions will contain an amount of active ingredient effective to achieve the desired result (e.g., decreasing the number of infected cells or infectious agents in a subject). For example, when administered in methods to treat an Parkinson's disease, such compositions will contain an amount of active ingredient effective to achieve the desired result (e.g., increasing the number of dopamine neurons or improving muscle control).

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of eliciting innate immune response as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring effectiveness and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

VI. Methods of Manufacture

In another aspect, there is provided a method of making a nucleic acid conjugate with structure S1. The method includes reacting a first oligonucleotide having up to about 200 bases with a carboxylic acid terminated, hydrophobic polymer, optionally in the further presence of a first linker, to afford a nucleic acid conjugate. Exemplary and non-limiting methods are disclosed in the Examples section.

VII. Methods of Delivery into a Target Cell

In another aspect, there is provided a method for delivery of an oligonucleotide into a target cell. The method includes administering an effective amount of a pharmaceutical composition as disclosed herein to a subject in need thereof.

VIII. Methods of Imparting Endonuclease Resistance

In another aspect, there is provided a method to impart endonuclease resistance to a first oligonucleotide, wherein the first oligonucleotide has a defined sequence. The method includes incorporating the first oligonucleotide into a nucleic acid conjugate as disclosed herein, and forming a micelle therefrom prior to exposure of the first oligonucleotide to an endonuclease. In one embodiment, the nucleic acid conjugate has the structure of any of S1, S2, S3, S4, S5, S6 or S7, as disclosed herein.

IX. Utility

Without wishing to be bound by any theory, it is believed that the disclosed compositions and methods can be used in a variety of ways, e.g., in cell cultures or animal models for functional studies on microRNA, gene therapy, for experiments to understand basic fundamentals of this area of biology and molecular genetics, as a tool for biomedical research, and the like. Use can be in vitro or in vivo for manipulations to understand how altering inhibiting genes or microRNA, in specific cells, affects a biological, biochemical, or genetic process.

It is further believed that the compositions and methods are useful for a variety of therapeutic applications. There are current clinical trials in effect for targeting microRNA (for example miR-122) in disease (e.g., Hepatitis C). The compounds and methods described here can target dopamine neurons, which are implicated in e.g., neurodegenerative disease (e.g., Parkinson's disease), addiction, mood disorder, and the like. MicroRNA are clearly implicated in some of the cellular and neuroanatomical processes of these diseases and the new technology described here can be employed for therapy. The targeting ligand can also be adapted for other cell types and diseases in other tissues and organ systems.

It is further believed that invention conjugates, micelles and targeted polymer nanoparticles are unique in the capability to deliver nucleic acids in vivo. This is the key hurdle in gene and nucleic acid therapies. That is, many systems have been proven in vitro, but few are amenable to widespread use in vivo.

In summary, there is disclosed a novel approach for rendering nucleic acids resistant to two key classes of nuclease that are otherwise capable of rapidly degrading substrates in a sequence selective or non-selective fashion.

Thus, there is disclosed methods for preparing nucleic acids that are resistant to nuclease driven degradation, yet which preserve the inherent sequence-selective binding and recognition properties of DNA. Nucleic acids were packed as DNA-polymer amphiphiles (DPAs) into micellar nanoparticles consisting of a high-density ssDNA corona with a hydrophobic organic polymer core. See e.g., Chien, M. P., et al., *Angew. Chem. Int. Ed.* 49:5076-5080; Hurst, S. J., et al., 2006, *Anal. Chem.* 78:8313-8318; Alemdaroglu, F. E. & Herrmann, A., 2007, *Org. Biomol. Chem.* 5:1311-1320. It is demonstrated that this morphology allows free access to additional complementary DNA strands while preventing and/or inhibiting the activity of various types of nucleases.

The methods and compounds disclosed herein provide inter alia the following benefits.

1. Specificity. Nucleic acids are delivered to the cell type that is desired, avoiding non-specific interactions, undesirable effects, and allowing for lower effective dosage. The external ligand can be modified to bind with the cell surface molecule of choice. Therefore, it is a modular platform for use in delivering a gene or nucleic acid of choice.

2. Non-toxicity. Zero toxicity of this compound was observed in neuronal cell cultures compared to ~10% cytotoxicity of a commercially available compounds.

3. Better presentation. Other compounds known in the art use cationic lipid chemistry and package the nucleic acid (e.g., DNA or RNA) inside the lipid micelle in an amorphous and poorly characterized fashion, whereas the composition disclosed herein carry the nucleic acid via covalent linkages specially designed to array the nucleic acid in a pre-determined manner, which allows for better intracellular presentation to the target molecule and resistance to unwanted interactions.

4. High adaptability. There are compositions known in the art that offer specificity, but those systems use antibodies as a means to confer specificity. The present disclosure employs a small molecule or an antibody and can be adapted accordingly. Antibodies are prone to immune activation, proteolysis, and are high molecular weight (and therefore high cost, or high mass-per-active-unit). In contrast, the present disclosure allows low molecular weight, lower cost, immune evasive, protection from proteolysis, protection from nucleases, and not opsonized in serum like antibody-based modalities as needed, and as necessary. It is a modular platform with respect to targeting.

Moreover, the present methods and compositions can be distinguished from commercially available compounds for nucleic acid delivery like Lipofectamine™, X-tremeGene Transfection Reagent, and from non-commercial formulations that use siRNA, cationic lipids, and antibodies for specificity. See, e.g., Yaworski E, U.S. Pat. No. 8,058,069; Wang T, et al. *Nanomedicine* (Lond). 2010 June; 5(4):563-74.

X. Examples

Example 1. DNA-Polymer Amphiphile Synthesis, Purification and Properties

General Methods

Reagents. All reagents were purchased from Sigma-Aldrich and used without further purification. (IMesH$_2$) (C$_5$H$_5$N)$_2$(Cl)$_2$Ru=CHPh was prepared as described by Sanford et. al (*Organometallics* 2001, 20:5314-5318). DNA synthesis was carried out on an ABI 394 DNA/RNA synthesizer utilizing standard phosphoramidite chemistry. DNA synthesis reagents and custom phosphoramidites were purchased from Glen Research Corporation. CPG support columns and standard phosphoramidites were purchased from Azco Biotech Inc. Nucleases Nt.CviPII and Exonuclease III were purchased from New England Biolabs. Phosphodiesterase I from *Crotalus adamanteus* was purchased from USB Corporation as a lyophilized powder. All deuterated solvents were purchased from Cambridge Isotope Laboratories Inc. $^1$H (400 MHz) and $^{13}$C (100 MHz) NMR spectra were recorded on a Varian Mercury Plus spectrometer. Chemical shifts ($^1$H) are reported in δ (ppm) relative to the CDCl$_3$ residual proton peak (7.27 ppm). $^{13}$C chemical shifts are reported in δ (ppm) relative to the CDCl$_3$ carbon peak (77.00 ppm). Mass spectra were obtained at the UCSD Chemistry and Biochemistry Molecular Mass Spectrometry Facility. Low-resolution mass spectra were obtained using a Thermo LCQdeca mass spectrometer and high-resolution mass spectra were obtained using an Agilent 6230 Accurate Mass time of flight mass spectrometer. Polymer molecular weight and polydispersity were determined via size-exclusion chromatography (Phenomenex Phenogel™ 5u 10, 1K-75K, 300× 7.80 mm in series with a Phenomenex Phenogel™ 5u 10, 10K-1000K, 300×7.80 mm (mobile phase: 0.05 M LiBr in DMF)) using a Hitachi LaChrom Elite® L-2130 pump equipped with a DAWN® HELEOS® multi-angle light scattering (MALS) detector (Wyatt Technology) and a refractive index detector (Hitachi L-2490) normalized to a 30,000 g/mol polystyrene standard. Hydrodynamic diameter (D$_h$) of DPA nanoparticles was measured via DLS using a DynaPro NanoStar (Wyatt Technology) instrument. DPA nanoparticle molecular weight was determined via batch mode SLS using a DAWN® HELEOS® MALS detector. Concentrations of oligonucleotides, DPA nanoparticles, and fluorescein phosphoramidite standards were determined using a Thermo Scientific NanoDrop 2000c spectrophotometer. HPLC analysis and purification of oligonucleotides was accomplished utilizing a Phenomenex Clarity® 5u Oligo-RP (150×4.60 mm) or Clarity 10u Oligo-WAX (150×4.60 mm) column and a Hitachi LaChrom Elite® L-2130 pump equipped with a UV-Vis detector (Hitachi LaChrom Elite® L-2420). Oligonucleotide molecular weights were determined by mass spectrometry performed on a Bruker Daltronics Biflex™ IV MALDI-TOF instrument using a combination of 2',4',6'-trihydroxyacetophenone monohydrate (THAP) and 3-hydroxypicolinic acid (3-HPA) as matrices and a three-point calibration standard (Oligonucleotide Calibration Standard #206200, Bruker). Denaturing polyacrylamide gel electrophoresis was performed using a Bio Rad Criterion Mini-PROTEAN® Tetra cell and precast TBE-Urea gels. Size-exclusion FPLC was accomplished using a HiPrep™ 26/60 Sephacryl® S-200 High Resolution-packed size-exclusion column (mobile phase: 10 mM Tris, 0.5 mM EDTA pH 8.3) and an Äkta purifier (Pharmacia Biotech) equipped with a P-900 pump and a UV-900 UV-Vis multiwavelength detector. TEM samples were deposited on carbon/formvar-coated copper grids (Ted Pella Inc.), stained with 1% w/w uranyl acetate, and imaged using a Tecnai™ G2 Sphera operating at an accelerating voltage of 200 kV. Fluorescence data were acquired using a Perkin Elmer HTS 7000 Plus Bio Assay Reader (excitation filter: IB14326, B126002, EX-A, emission filter: IB21654, B126103, EM-A). DNA melting temperature analysis was conducted using a Beckman Coulter DU 640 spectrophotometer equipped with a high performance temperature controller. Enzyme kinetics were calculated using Lineweaver-Burk plot analysis with enzyme concentrations determined via a standard Bradford assay, as known in the art.

Abbreviations. Abbreviations used herein, as known in the chemical arts, include the following: HATU: 2-(7-Aza-1H-Benzotriazole-1-yl)-1,1,3,3-tetramethyluronium hexafluorophosphate; DIPEA: di-isopropyl ethyl amine; DMF: dimethylformamide; NMR: nuclear magnetic resonance; $CDCl_3$: deuterated chloroform; h: hour; rt: room temperature; TEM: transmission electron microscopy; MALDI-TOF: matrix assisted laser desorption/ionization time of flight mass spectrometry; HPLC: high performance liquid chromatography; THAP: 2',4',6'-trihydroxyacetophenone monohydrate; 3-HPA: 3-hydroxypicolinic acid; MALS: multi-angle light scattering; DPA: DNA-polymer amphiphile; NHS: N-hydroxysuccinimide; HMPA: hexamethylphosphoramide linking reagent; DMT: 4,4'-dimethoxytrityl; DMTO: 4,4'-dimethoxytrityl with oxygen; DCM: dichloromethane; THF: tetrahydrofuran; SEC-MALS, size exclusion chromography—multiangle laser light scattering; DABCYL, 4-(dimethylaminoazo) benzene-4-carboxylic acid.

Monomer and Termination Agent Synthesis (N-Benzyl)-5-norborene-exo-2,3-dicarboximide. (1). Compound 1 was prepared according to previously reported procedure. See Ku, T. H. et al., 2011, *J. Am. Chem. Soc* 133:8392-8395. To a stirred solution of N-benzylamine (2.85 g, 26.6 mmol) in dry toluene (125 mL) was added 5-norbornene-exo-2,3-dicarboxylic anhydride (4.10 g, 25.0 mmol) and triethylamine (3.83 mL, 27.5 mmol). The reaction was heated to reflux overnight under an atmosphere of $N_2$. The reaction was cooled to room temperature and washed with 10% HCl (3×50 mL) and brine (2×50 mL). The aqueous layers were combined and extracted with ethyl acetate (60 mL). The combined organic layers were dried with $MgSO_4$, filtered and concentrated to dryness yielding a pale yellow solid that was then recrystallized from ethyl acetate/hexanes to give 1 (4.98 g, 79%) as white crystals. $^1$H NMR ($CDCl_3$): δ (ppm) 1.07 (d, 1H, $CH_2$, J=9.6 Hz,), 1.42 (d, 1H, $CH_2$, J=9.6 Hz), 2.69 (s, 2H, 2×CH), 3.26 (s, 2H, 2×CH), 4.61 (s, 2H, $CH_2$), 6.28 (s, 2H, CH═CH), 7.25-7.40 (m, 5H, Ar). $^{13}$C NMR ($CDCl_3$): δ (ppm) 42.18, 42.28, 45.13, 47.62, 127.74, 128.48, 135.76, 137.76, 177.48. LRMS (CI), 253.99 [M+H]$^+$. HRMS, theo: 254.1176 [M+H]$^+$, found: 254.1175 [M+H]$^-$.

(Z)-4,4'-(but-2-ene-1,4-diylbis(oxy))dibenzoic acid (2). To a stirred solution of ethyl 4-hydroxybenzoate (5.5 g, 33.1 mmol) in 100 mL dry DMF was added potassium carbonate (7.28 g, 52.7 mmol). To this stirred suspension was added cis 1,4-dichlorobutene (2.0 g, 16 mmol). The solution turned brown within minutes and the reaction was allowed to stir under an atmosphere of $N_2$ at 90° C. overnight. The mixture was then cooled to room temperature, filtered, and concentrated to dryness. The resulting solid was dissolved in ethyl acetate and washed three times with $H_2O$. The organic layer was dried over magnesium sulfate and concentrated to dryness to yield solid white crystalline needles. This solid was recrystallized from ether to yield the pure diester (2.18 g, 35%). $^1$H NMR ($CDCl_3$): δ (ppm) 1.38 (t, 6H, 2×$CH_3$), 4.35 (q, 4H, 2×$CH_2$), 4.74 (d, 4H, 2×$CH_2$), 5.96 (t, 2H, CH═CH), 6.92 (d, 4H, 4×ArH), 8.0 (d, 4H, 4×ArH). The diester (2.18 g, 5.66 mmol) was dissolved in 95% ethanol and potassium hydroxide was added (12.0 g, 215 mmol). The reaction was heated to reflux for 5 hours, cooled to room temperature, diluted with an equal volume of $H_2O$ and acidified with HCl to form a white precipitate. The precipitate was filtered off to yield 2 as an orange-tan solid (1.78 g, 100%). $^1$H NMR (DMSO-d6, residual $^1$H=2.50 ppm): δ (ppm) 3.38 (s broad, 2H, 2×COOH), 4.80 (d, 4H, 2×$CH_2$), 5.89 (t, 2H, CH═CH), 7.03 (d, 4H, 4×ArH), 7.87 (d, 4H, 4×ArH). $^{13}$C NMR (DMSO-d6, residual $^{13}$C=39.51 ppm): δ (ppm) 64.11, 114.50, 123.18, 128.33, 131.34, 161.72, 166.98. LRMS, 327.03 [M–H]$^-$, HRMS, theo: 327.0874 [M–H]$^-$, obs: 327.0877 [M–H]$^-$.

Polymer Synthesis Via Ring-Opening Metathesis Polymerization (ROMP)

Figure 4:
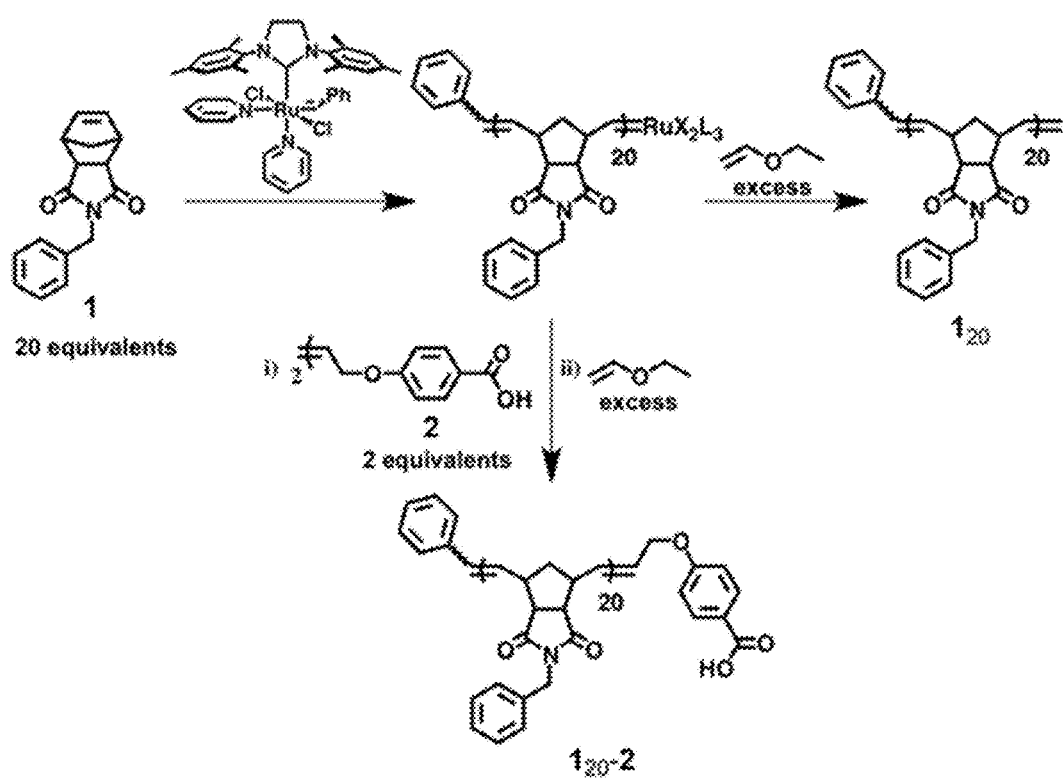
FIG. 4 depicts schematic of carboxylic acid-terminated polymer synthesis via ROMP. Compound $1_{20}$ is a homopolymer aliquot for phenyl block $M_n$ determination.
Figure 5:
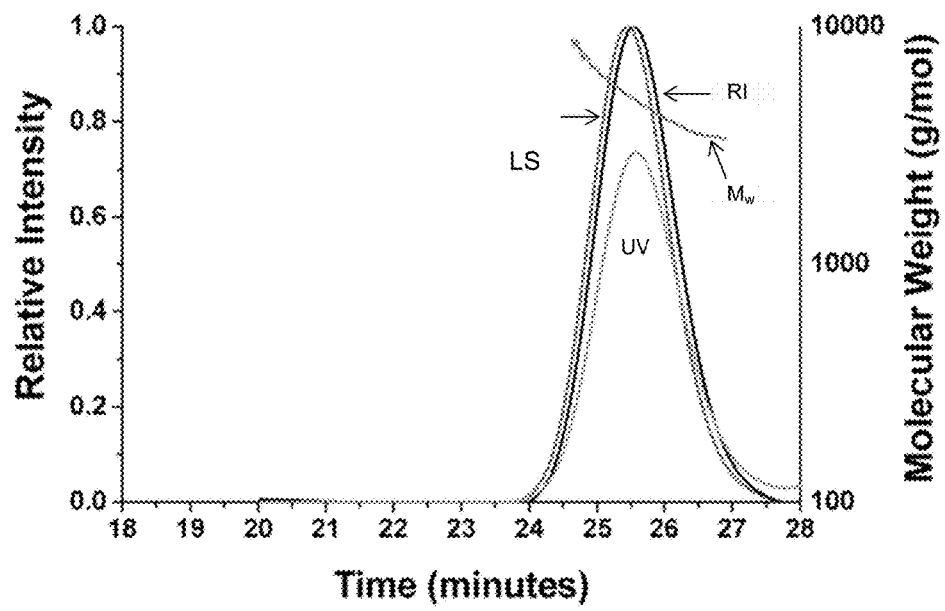
FIG. 5 depicts Polymer $1_{20}$ SEC-MALS chromatogram (LS=light scattering Rayleigh ratio, RI=refractive index difference, UV=UV absorbance at 280 nm, Mw=polymer molecular weight).
Figure 6:
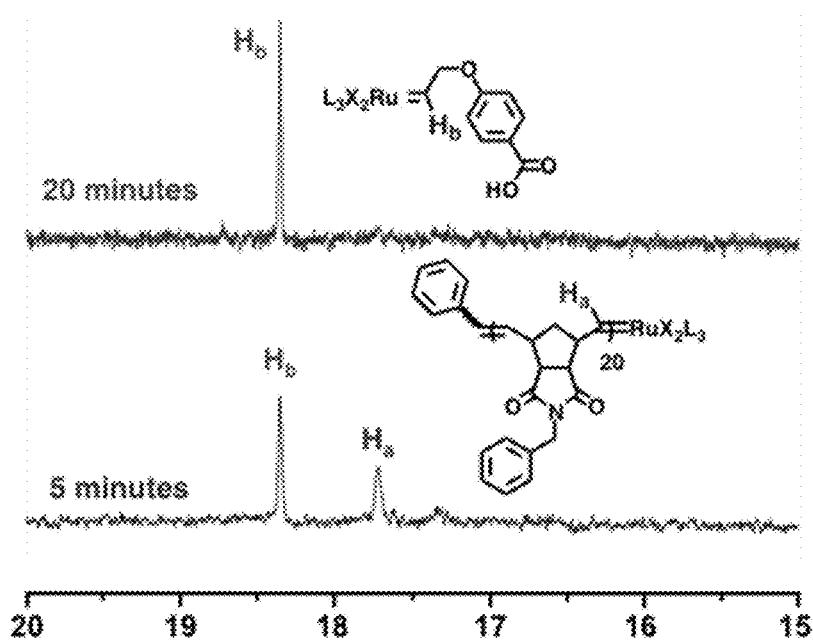
FIG. 6 depicts $^1$H-NMR overlay showing complete termination of ROMP polymer with termination agent 2 (x-axis=δ in ppm). The resonance of the alkylidine proton in the polymeric species is at 17.7 ppm. Upon termination with compound 2, an alkylidine proton resonance corresponding to the metathesis product appears at 18.4 ppm. At 20 minutes, the resonance corresponding to the polymeric species is absent, indicating completion of the polymer termination reaction. At this point ethyl vinyl ether can be added to quench the catalyst.

Polymer ($1_{20}$-2)— as shown in the scheme of FIG. 4. Monomer 1 (870 mg, 3.4 mmol) was dissolved in 5 mL $CDCl_3$ and cooled to −78° C. Ruthenium catalyst (IMesH$_2$)($C_5H_5N$)$_2$(O)$_2$Ru═CHPh (124 mg, 0.17 mmol) was added as a powder, followed by 1 mL additional $CDCl_3$ to solubilize the catalyst. The reaction was then allowed to warm to room temperature and stir under $N_2$ for 35 minutes (NMR confirms the absence of the original olefin resonance from monomer 1 at 6.28 ppm, and the presence of broad cis and trans polymer backbone olefin resonances at 5.45 and 5.71 ppm). At this point, 200 µL of the reaction mixture was removed and quenched with an excess of ethyl vinyl ether to provide a homopolymer for molecular weight determination (SEC-MALS: $M_n$=5221 g/mol, PDI=1.075, FIG. 5). Termination agent 2 (111 mg, 0.34 mmol) was dissolved in 2.0 mL DMF-d7, added to the reaction mixture, and the mixture was allowed to stir at room temperature for 20 minutes. The ruthenium alkylidene proton resonance was monitored in order to track the completion of the polymer termination event (FIG. 6). Once termination was determined to be complete, excess ethyl vinyl ether was added to quench the ruthenium catalyst. The crude polymer was precipitated from cold methanol and further purified by column chromatography in order to eliminate any traces of unreacted termination agent. The crude precipitated polymer was dry loaded onto a silica column, the column was washed with 200 mL $CH_2Cl_2$, and the polymer was eluted with 3% methanol in $CH_2Cl_2$ to yield a glassy yellow-brown solid as the pure polymer (905 mg, 97%, rf=0.56).

DNA Synthesis

Figure 7:
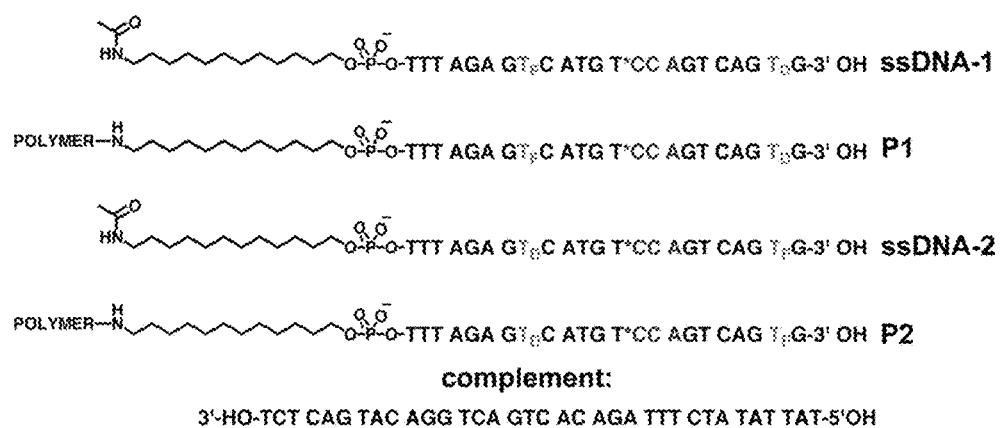
FIG. 7 depicts DNA sequences and chemical modifications. The recognition site for Nt.CviPII is indicted in red and the nick site is indicated by an asterisk. Sequence legend: ssDNA-1 (SEQ ID NO:2); P1 (SEQ ID NO:2); ssDNA-2 (SEQ ID NO:3); P2 (SEQ ID NO:3); complement (SEQ ID NO:4).

Oligonucleotides ssDNA-1 and ssDNA-2 were synthesized in house using automated phosphoramidite chemistry and saccharin 1-methylimidazole as an activator. Standard 2-cyanoethyl protected phosphoramidites include dA (N-Bz), dG (N-dmf), (N-acetyl) dC, and T. Oligonucleotides were synthesized on a 1.0 µmol scale using columns packed with 1000 Å CPG beads. A 5'-amino modifier was incorporated into each synthetic oligonucleotide through use of 5'-amino modifier Cl2 phosphoramidite (Glen Research). In the case of ssDNA-1 and ssDNA-2, the 5'-amino terminus was acetylated on solid support using the automated synthesizer. The MMT group was removed by treatment with 3% trichloroacetic acid in $CH_2Cl_2$ for two minutes (until the yellow color due to the MMT cation was no longer visible in the eluting deblock solution) followed by a standard capping cycle to acetylate the free amine with acetic anhydride. Fluorescein and DABCYL labels were incorporated into the oligonucleotides via use of Fluorescein dT and DABCYL dT phosphoramidites (Glen Research). Oligos were cleaved from solid support and deprotected by treatment with AMA (concentrated $NH_4OH$/40% methylamine, 1:1 v/v) at 55° C. for 20 minutes, purified by HPLC, and characterized by MALDI-TOF MS. Target DNA was purchased from Integrated DNA Technologies (purified by HPLC, confirmed by ESI-MS). Detailed sequences and enzyme recognition/cleavage sites are shown in FIG. 7.

HPLC Purification of Oligonucleotides

Figure 8A:
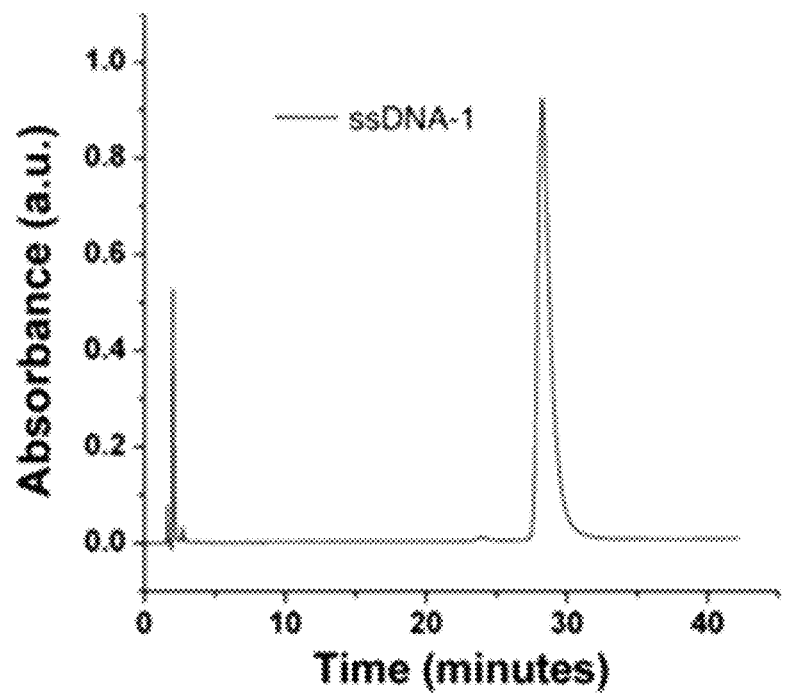
FIGS. 8A-8D depict HPLC purification and MALDI-TOF analysis of ssDNA-1 and ssDNA-2.
Figure 8B:
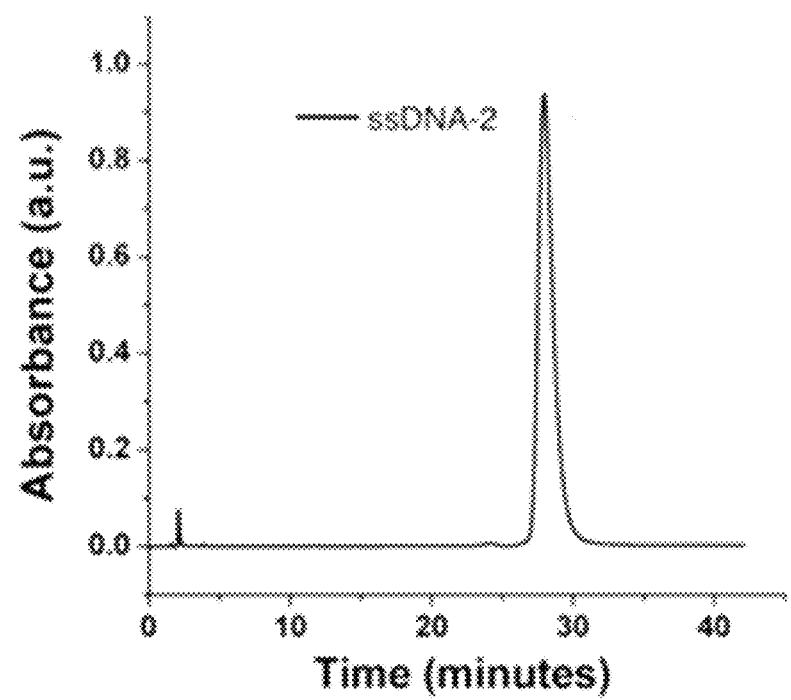

Synthetic oligonucleotides ssDNA-1 and ssDNA-2 were purified via reverse-phase HPLC using a binary gradient as indicated, e.g., on each chromatogram in FIGS. 8A-8B (Solvent A: 10% methanol in 50 mM triethylammonium acetate (TEAA) pH 7.1, solvent B: methanol). For ssDNA-2, weak anion-exchange (WAX) HPLC was also necessary to purify the oligonucleotide. A quaternary gradient was used for WAX HPLC analysis and purification (Solvent A: Nanopure® $H_2O$, solvent B: methanol, solvent C: 100 mM Tris(hydroxymethyl)aminomethane (Tris) pH 8.0, solvent D: 2 M NaCl). Oligonucleotides were desalted post WAX HPLC purification using Sep-Pak Plus C18 Environmental Cartridges.

MALDI-TOF MS of Oligonucleotides

Figure 8C:
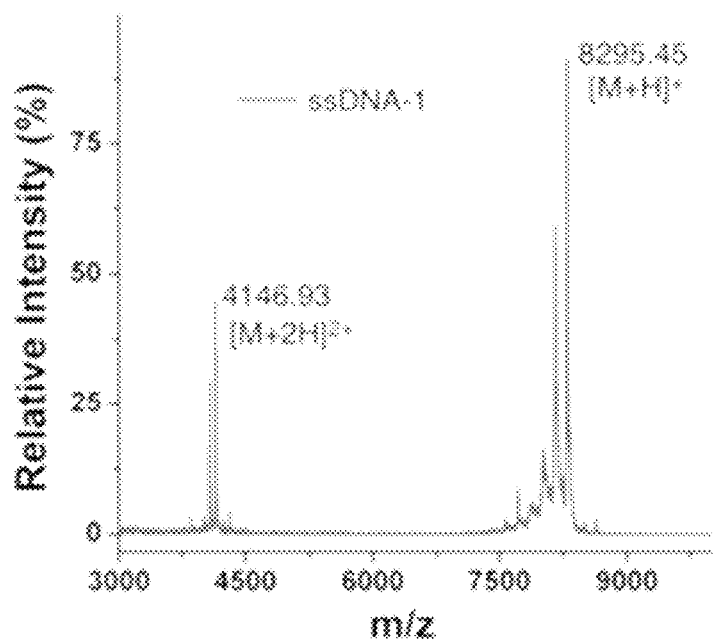
Figure 8D:
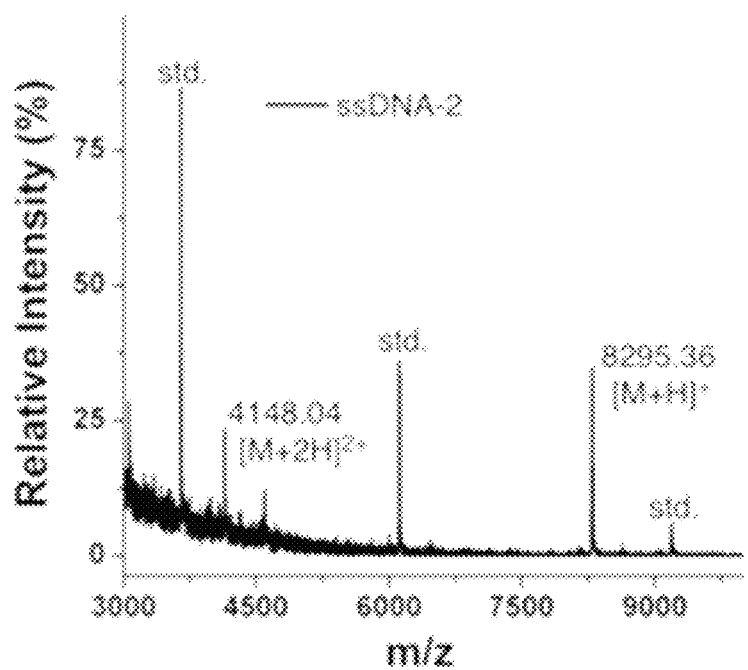

A MALDI target plate was spotted with 1 µL of matrix solution A for each sample to be analyzed and waiting 20 minutes for the solution to dry (matrix solution A was prepared by dissolving 50 mg of 3-HPA in 500 µL of HPLC acetonitrile/Nanopure® $H_2O$ (1:1 v/v). 454 µL of this solution was mixed with 45 µL of 100 mg/ml diammonium hydrogen citrate in Nanopure® $H_2O$). Oligonucleotide samples were prepared for MALDI-TOF MS analysis using Zip-Tip C18 pipette tips. Oligos were loaded onto the C18 tips from concentrated stock solutions (ca. 50-100 µM) and eluted with matrix solution B (matrix solution B was prepared as follows: dissolve 50 mg of THAP in 500 µL of HPLC grade acetonitrile, assist dissolution by sonication and centrifuge the resulting solution to pellet any solid remaining, mix 250 µL of the supernatant with 250 µL of 23 mg/mL diammonium hydrogen citrate in Nanopure® $H_2O$). 1 µL of the oligonucleotide in matrix solution B was mixed with 1 µL of Oligonucleotide Calibration Standard dissolved in Nanopure® $H_2O$ (Bruker). 1 µL of this solution was then spotted onto the MALDI plate on top of crystallized matrix A. The samples were allowed to dry for 15-30 minutes before analyzing via MALDI-TOF MS. See FIGS. 8C-8D.

DNA-Polymer Amphiphile Synthesis and Purification

Synthesis.

To a solution of polymer ($1_{20}$-2) (150 mg, 27.8 µmol) dissolved in 250 µL DMF was added N,N-diisopropylethylamine (48 µL, 280 µmol) and HATU (10.6 mg, 28 µmol). The solution was vortexed for 10 minutes at room temperature in order to activate the polymer carboxylic acid terminus. At this point, 5'-amino modified DNA on CPG solid support (ca. 1 µmol, MMT deprotected) was added. The mixture was allowed to vortex at room temperature overnight. The CPG beads were filtered away from the solution using an empty synthesis column and then washed with DMF (2×20 mL) and $CHCl_3$ (2×20 mL). The DPA was cleaved from solid support via treatment with AMA at 65° C. for 30 minutes. The CPG beads were filtered off using glass wool and subsequently washed consecutively with $H_2O$ (2.0 mL), DMSO (2.0 mL), Formamide (2.0 mL), $H_2O$ (3.0 mL), and DMSO (1.0 mL). This solution was transferred to 3,500 MWCO snakeskin dialysis tubing (Thermo Scientific) and 2.0 mL $H_2O$, used to wash the filtrate container, was added. The resulting solution was dialyzed against 2.0 L of Nanopure® $H_2O$ overnight. This dialyzed solution was then concentrated to 3.0 mL via SpeedVac® evaporation before purifying via SEC FPLC.

Purification.

Figure 9A:
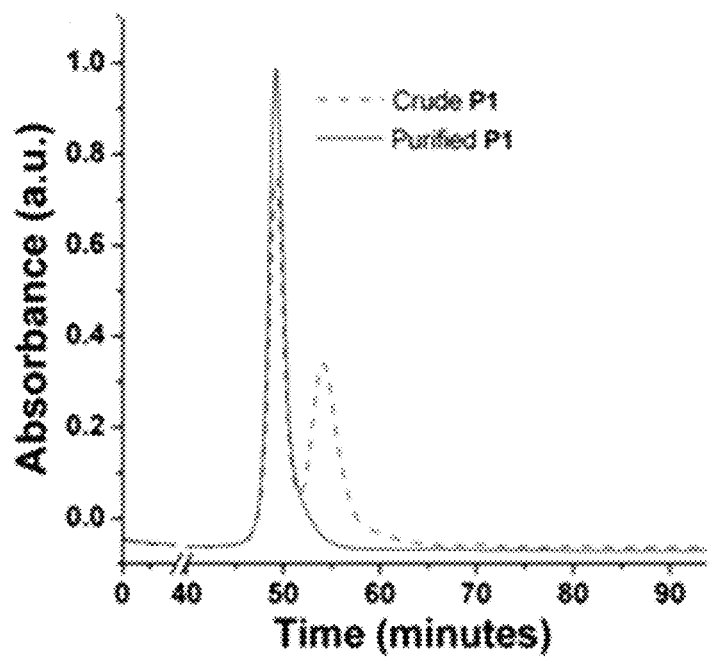
FIGS. 9A-9B depict SEC FPLC purification of DPA nanoparticles P1 (FIG. 9A) and P2 (FIG. 9B). Legend: crude P1 or P2 (broken line); purified P1 or P2 (solid line).
Figure 9B:
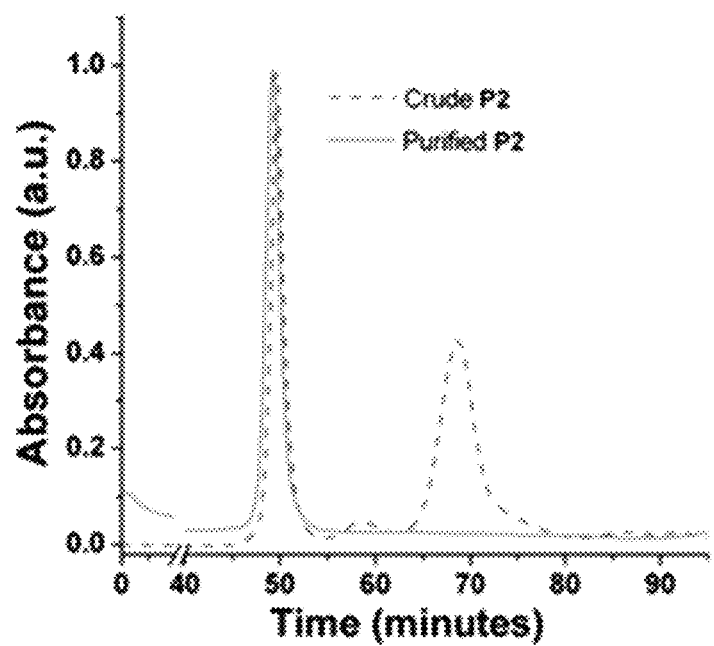
Figure 10A:
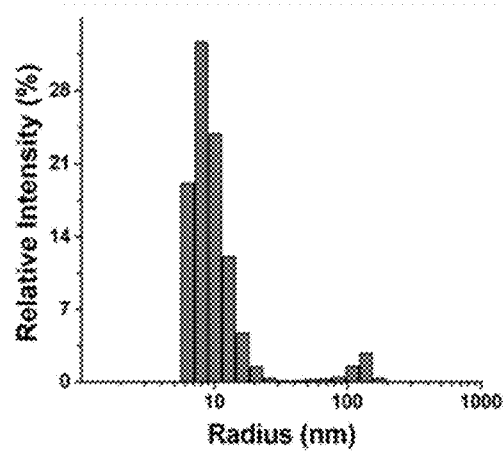
FIGS. 10A-10E depict light scattering data for DPA nanoparticles P1 and P2.
Figure 10B:
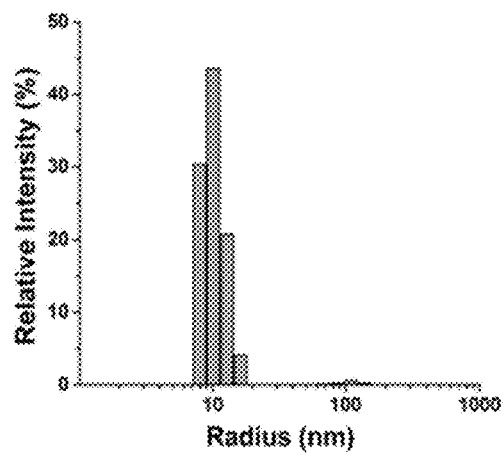
Figure 10C:
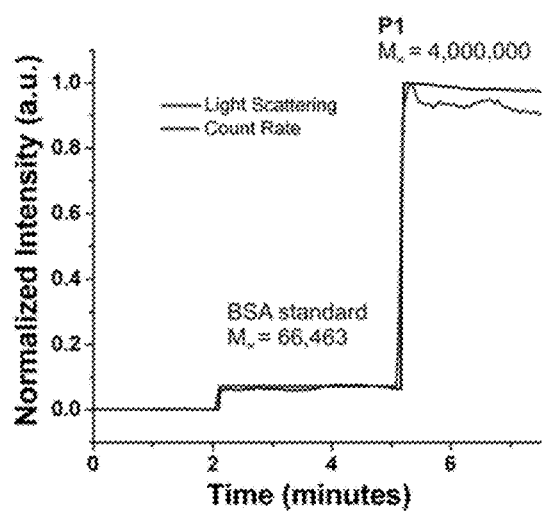
Figure 10D:
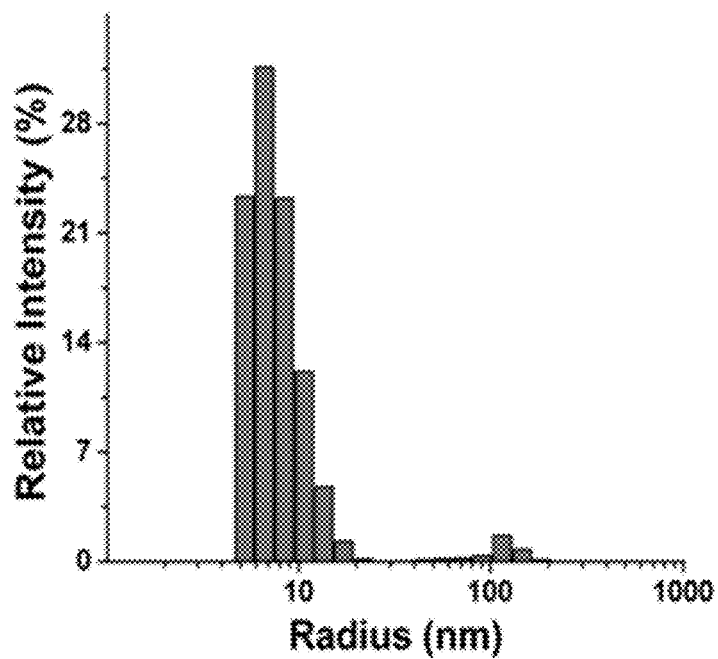
Figure 10E:
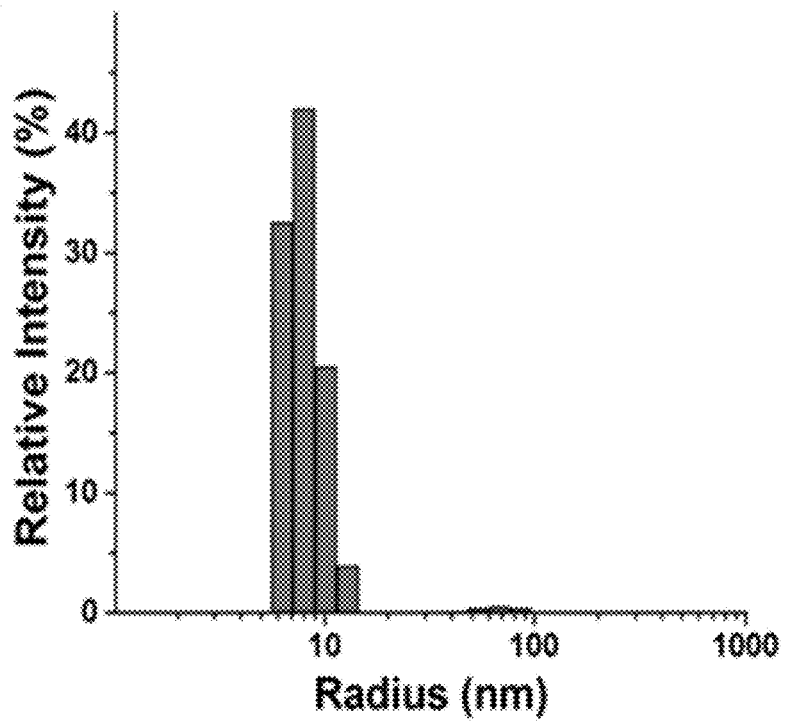

The resulting crude DPA/ssDNA mixture was analyzed by denaturing PAGE and agarose gel electrophoresis to confirm the presence of conjugate and free ssDNA. It is important to note that low molecular weight ssDNA impurities (≤8295 g/mol) remained present despite extensive dialysis attempts (20 k MWCO Slide-a-Lyzer® dialysis cassette). This crude mixture was purified via SEC FPLC (mobile phase: 10 mM Tris, 0.5 mM EDTA pH 8.3, flow rate: 2 ml/min, $\lambda_{abs}$=260 nm). The DPA nanoparticles elute at ca. 50 minutes (FIGS. 9A-9B). If left as a crude mixture for an extended period of time (approx. 1 month), ssDNA+impurities will aggregate and thus shift to an earlier elution time. Crude P1 sample was purified using HiLoad™ 16/60 Superdex™ 200 prep grade SEC media and, therefore, the DPA exhibits a retention time differing from that of pure P1. All subsequent purifications and reinjections of pure material were performed using HiPrep 26/60 Sephacryl S-200 High Resolution SEC media.

Transmission Electron Microscopy (TEM)

Copper grids (formvar/carbon-coated, 400 mesh copper, Ted Pella #01754) were prepared by glow discharging the surface at 20 mA for 1.5 minutes followed by treatment with 3.5 µL 250 mM $MgCl_2$ in order to prepare the surface for DPA nanoparticle adhesion. The $MgCl_2$ solution was wicked away with filter paper and 3.5 µL of DPA nanoparticle (ca. 50 µM DNA in 10 mM Tris pH 8.5) solution was deposited on the grid surface. This solution was allowed to sit for 5 minutes before being washed away with 4 drops of glass distilled $H_2O$ and subsequent staining with 3 drops of 1% w/w uranyl acetate. The stain was allowed to sit for 30 seconds before wicking away with filter paper. All grid treatments and sample depositions were on the dark/shiny/glossy formvar-coated face of the grid (this side face up during glow discharge). Samples were then imaged via TEM.

DNA Concentration Determination

Nucleic acid concentrations were determined by UV absorbance at 260 nm using a quartz cuvette (Fisher #14-385-928A, pathlength=10 mm). An extinction coefficient of 294,554.58 L/mol·cm was used for ssDNA-1, ssDNA-2, P1, and P2. This coefficient was calculated as the extinction coefficient of the entire sequence without the two thymine modified bases (226,654.58 L/mol·cm, OligoCalc) plus the extinction coefficients for each dye-labeled base at 260 nm (38,800 L/mol·cm for Fluorescein dT, and 29,100 L/mol·cm for DABCYL dT, Glen Research). Due to the fact that P1 and P2 contain additional aromatic groups capable of absorbing UV radiation, a slight correction factor was introduced. This correction factor was calculated as the ratio of absorbance of ssDNA-1 or ssDNA-2 at 492 nm versus 260 nm ($A_{260}/A_{492}$). This correction factor was multiplied by P1 or P2 absorbance at 492 nm in order to calculate what the absorbance at 260 nm would be if the system behaved as the standard ssDNA analogues. This corrected absorbance at 260 nm was then averaged with the actual DPA-nanoparticle absorbance at 260 nm and used to determined nucleic acid concentration. For example, P1 $A_{260}$=0.168 (0.57 µM) and $A_{260\ corrected}$=0.130 (0.44 µM). Therefore, $A_{260\ average}$= 0.149 (0.50 µM).

Gel Electrophoresis

Denaturing PAGE was accomplished using Bio-Rad Criterion 15% TBE-Urea precast gels (#345-0091) and loading 200 ng of DNA per lane for each sample to be analyzed. In the case of crude conjugate, 400 ng of DNA was loaded per lane. Samples were prepared to load by mixing 1:1 (v/v) with TBE-Urea Sample Buffer (#161-0768, Bio-Rad) and heating to 90° C. for 2 minutes followed by rapid cooling on ice. The gels were run in 1× Tris/Boric Acid/EDTA (TBE) buffer pH 8.4 at 200V for 70 minutes, stained with ethidium bromide (200 ng/L) for 30 minutes and visualized using a Bio-Rad Fluor-S MultiImager.

Fluorescence Measurements

Figure 11:
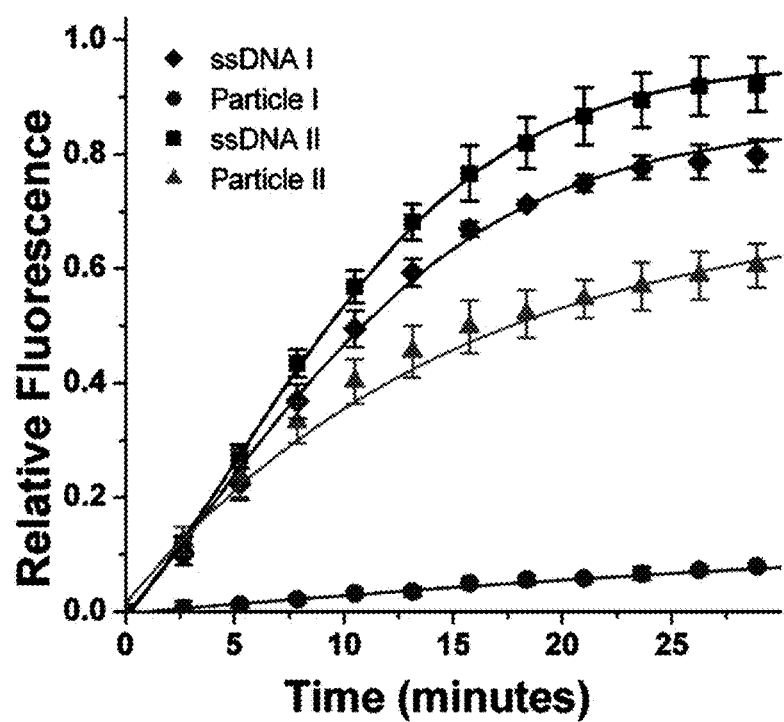
FIG. 11 depicts DPA-nanoparticle resistance to snake venom phosphodiesterase (SVP). SVP activity over time was monitored by fluorescein fluorescence dequenching ($\lambda_{ex}$=485 nm, $\lambda_{em}$=535 nm). Legend: ssDNA-1 (diamond); P1 (circle); ssDNA-2 (box); P2 (triangle).
Figure 12A:
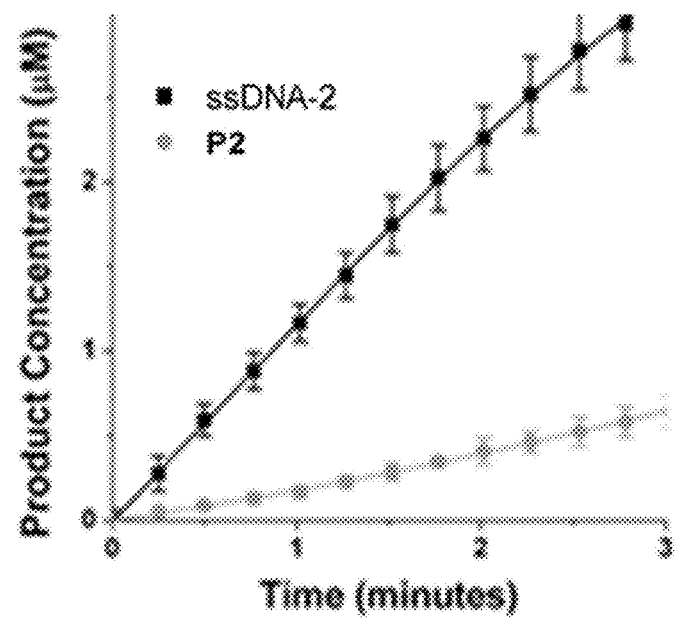
FIGS. 12A-12G depict ExoIII kinetic analysis against ssDNA-2 and P2. See Table 1.
Figure 12B:
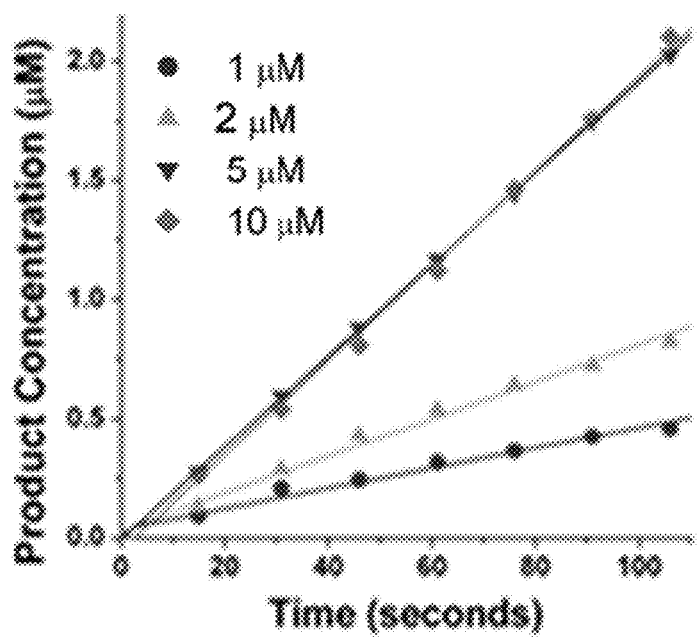
Figure 12C:
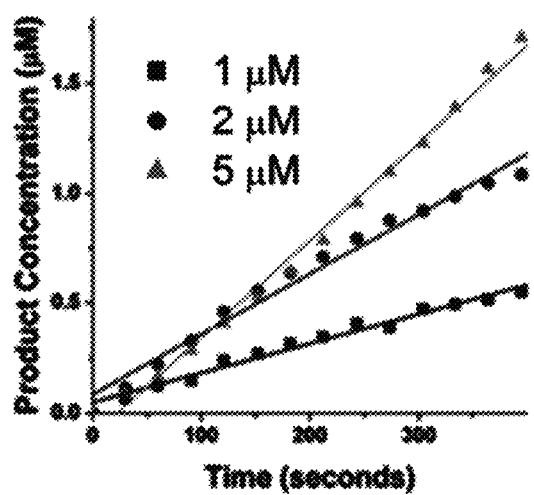
Figure 12D:
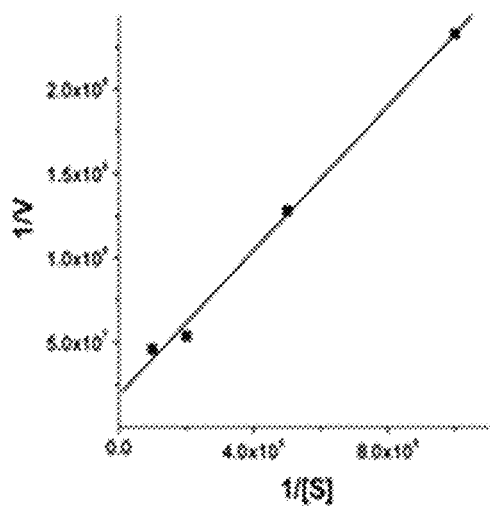
Figure 12E:
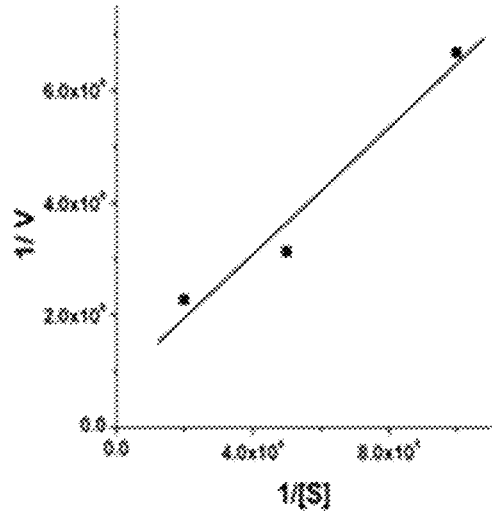
Figure 12F:
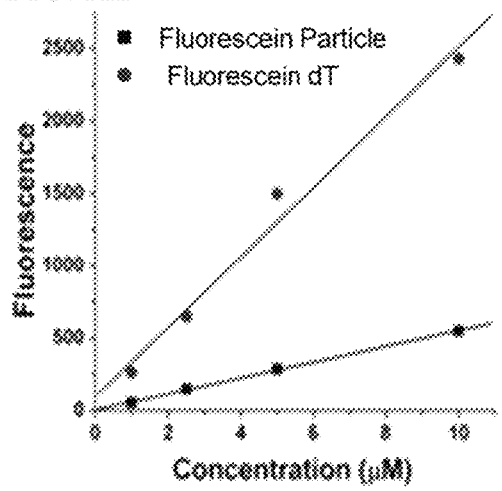
Figure 12G:
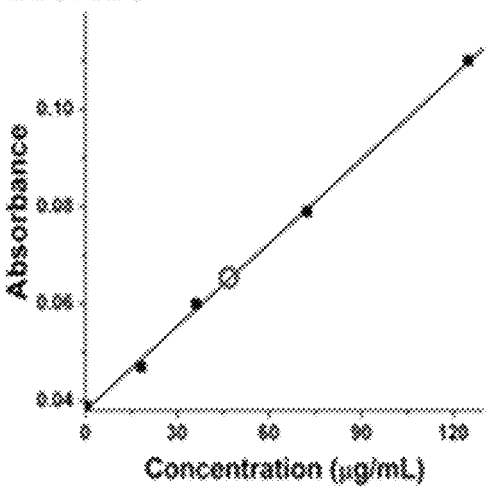
Figure 13A:
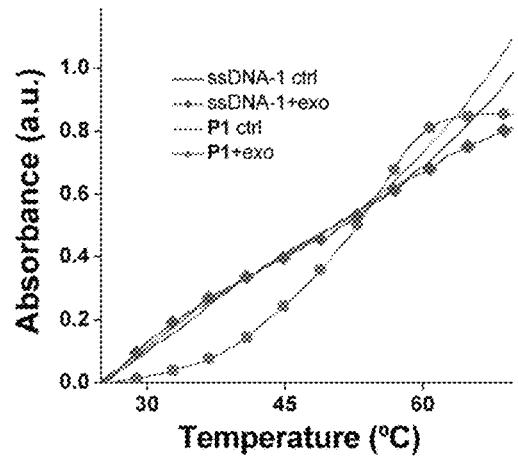
FIGS. 13A-13B depict DNA melting temperature analysis with and without ExoIII treatment.
Figure 13B:
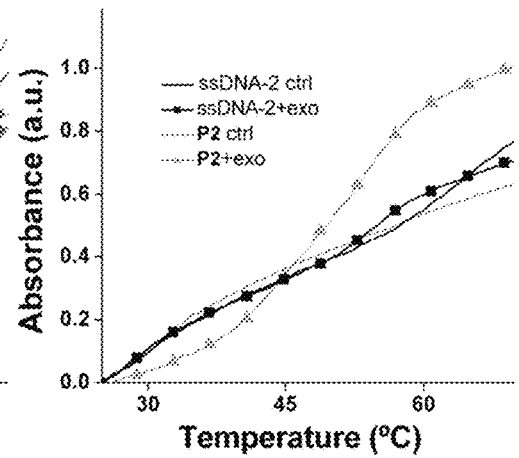

Each experiment was measured in triplicate and plotted as a normalized average (i.e. time point zero was set to zero fluorescence) with standard deviation plotted as error bars. Sigmoidal fits were performed for each data set. Fluorescein fluorescence de-quenching was monitored over time using a plate-reader and a 96 well plate (Corning, flat bottom non-binding surface #29110009). Time points were collected in 15-second intervals integrating three flashes per measurement. Identical gain and filter settings were used in every case. For measuring Nt.CviPII activity, the following conditions were used in each experiment: 5 µM ssDNA or DPA-nanoparticle, 300 nM ssDNA complement, 25 mM NaCl, 1× NE Buffer 4, 10 mM Tris pH 8.5, and 5 units of Nt.CviPII (100 units in 20 µL was diluted to 100 µL with 80 µL of Diluent A, 5 µL of this solution was used per reaction) all in 50 µL total volume. NE Buffer 4 and enzyme were mixed and added to each well. All other components were mixed and added to each enzyme/buffer-containing well simultaneously using a multi-channel pipettor. The plate reader was set to 37° C. for the duration of the 100 minute experiment. For measuring ExoIII activity, the following conditions were used in each experiment: 5 µM ssDNA or DPA-nanoparticle, 25 mM NaCl, 50 mM Potassium Acetate, 1× NE Buffer 1, 10 mM Tris pH 8.5, and 10 units of ExoIII (5,000 units in 50 µL was diluted to 500 µL with 450 µL of Diluent A, 1 µL of this solution was used per reaction) all in 50 µL total volume. NE Buffer 1 and enzyme were mixed and added to each well. All other components were mixed and added to each enzyme/buffer-containing well simultaneously using a multi-channel pipettor. The plate reader was set to 37° C. for the duration of the 60 minute experiment. For measuring SVP activity (FIG. 11), the following conditions were used in each experiment: 5 µM ssDNA or DPA-nanoparticle, 25 mM NaCl, 50 mM Potassium Acetate, 12.5 mM $MgCl_2$, 10 mM Tris pH 8.5, and 0.6 units of SVP (1.58 mg of lyophilized SVP powder (63 units/mg) was dissolved in 1.58 mL of buffer containing 100 mM Tris-HCl, pH 8.9, 110 mM NaCl, 15 mM $MgCl_2$, and 50% glycerol, 10 µL of this solution was used per reaction) all in 50 µL total volume. $MgCl_2$ and enzyme were mixed and added to each well. All other components were mixed and added to each enzyme/buffer-containing well simultaneously using a multi-channel pipettor. The plate reader was set to 37° C. for the duration of the 60 minute experiment.

DNA Melting Temperature Analysis

Melting temperature analysis were performed by heating each sample from 25° C. (5 minute equilibration time) to 70° C. using a temperature gradient of 1° C./minute. Melting temperatures were calculated as first derivatives of the curve. Each strand was at a concentration of 0.83 µM. For melting analysis after Nt.CviPII treatment, the reaction mixture was heated to 70° C. for 20 minutes in order to denature the enzyme. The mixture was then cooled to room temperature and 228.1 µL of 10 mM Tris pH 8.5 was added, followed by 12.5 µL 2M NaCl and 9.4 µL of 24.8 µM complementary DNA in 10 mM Tris pH 8.5. Final concentrations of each strand are 0.83 µM and final NaCl concentration is 87.5 mM all in a total volume of 300 µL. At this point, the sample was heated at 90° C. for 5 minutes and then allowed to cool to room temperature over a period of 2 hours. The sample was refrigerated at 8° C. for 15 minutes and subsequently analyzed. For melting temperature analysis after ExoIII treatment, after the reaction was complete (60 minutes), 10 µL of 0.5 M EDTA was added to inhibit the enzyme. The reaction was heated at 70° C. for 20 minutes and allowed to cool to room temperature. 217.5 µL of 10 mM Tris, followed by 12.5 µL of 2M NaCl and 10 µL of 24.8 µM complementary DNA was added. At this point the sample was treated identical to those in the case of Nt.CviPII.

Results and Discussion

Figure 1B:
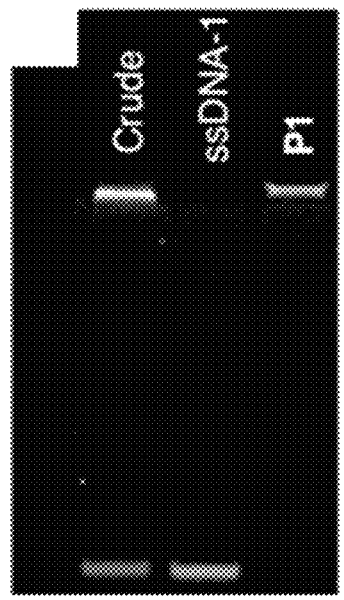
Figure 1C:
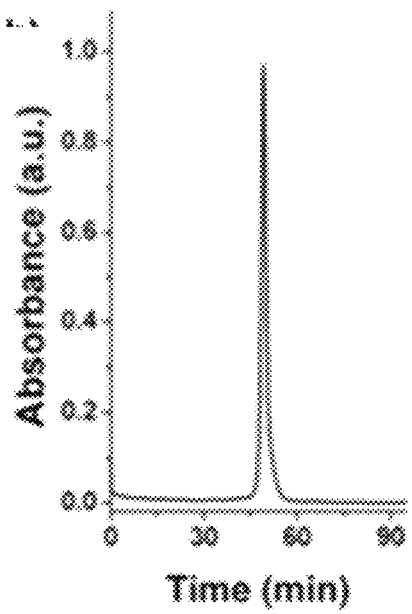
Figure 1D:
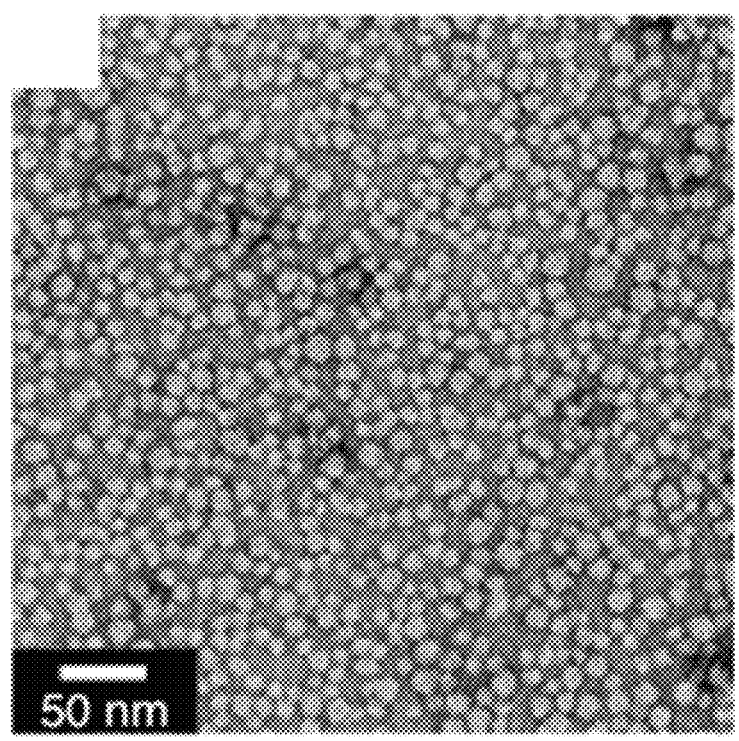

DPAs were prepared via conjugation of a hydrophobic polymer, terminally modified with a carboxylic acid moiety, to a 5'-amino-modified oligonucleotide on solid support. See e.g., FIG. 1A. The resulting DNA-polymer conjugate was separated from unreacted polymer by rinsing the support, followed by cleavage and dialysis to give a mixture of spherical micellar nanoparticles and free, unreacted single-stranded DNA (ssDNA, FIG. 1B, lanes 2-3). The particles were separated from ssDNA via size-exclusion chromatography (SEC-FPLC) to give purified material (FIGS. 1B-1C). This procedure was utilized in the preparation of two well-defined micellar nanoparticles, P1 and P2, both on the order of 20 nm in diameter, with low polydispersity as determined by TEM (FIG. 1D), and light scattering. Static light scattering (SLS) was utilized to confirm aggregation numbers (Nagg) on the order of 200 DNA strands per particle. See FIGS. 10A-10E. Therefore, nucleic acids at high densities of approximately 0.2 DNA strands/$nm^2$ on the surface of the micelles can be obtained. See Hurst, S. J., et al., 2006, Id. See Rush, A. M., et al., *ACS Nano* 2013, 7:1379-1387.

The two particles (P1 and P2) were designed to incorporate substrates for several types of nuclease; specifically, a selective endonuclease together with indiscriminate exonucleases. To monitor nuclease activity, two similar particles were prepared differing only in the location of dye- and quencher-labels incorporated as thymine-modified phosphoramidites during nucleic acid synthesis. ssDNA-1 consists of a DABCYL-modifier located towards the 3'-terminus, and a fluorescein-modifier bases away towards the 5'-terminus. See e.g., Xia, Y. N., et al., 1988, *Nucl. Acids Res*

16:9477-9487. By contrast, ssDNA-2 has the reverse arrangement with a fluorescein-modifier towards the 3'-terminus. This pair of sequences was designed to detect nuclease activity via the release of free fluorescein (ssDNA-1), or free quencher (ssDNA-2) from the 3'-terminus (vide infra). The two sequences were incorporated as DPAs to generate the two particles, and in addition were purified with-out polymer conjugation as ssDNA analogues as controls.

To examine how DPA nanoparticles respond as substrates to sequence selective endonucleases, a substrate for nicking endonuclease Nt.CviPII was incorporated. The recognition and cleavage site for the enzyme was placed between fluorescein and DABCYL-labeled thymidine moieties of each oligonucleotide in order to study the kinetics of the enzyme-catalyzed cleavage via increased fluorescence upon de-quenching. Nt.CviPII is a nicking endonuclease that recognizes double-stranded DNA (dsDNA) and introduces a single-strand break on the 5' side of the recognition sit. See e.g., Xia, Y. N., et al., 1988, Id. The system was designed such that nucleolytic cleavage occurs on the sequence of the DPA nanoparticle or ssDNA analogue while leaving the complementary target sequence fully intact. Without wishing to be bound by any theory, it was reasoned that this design would facilitate a catalytic degradation of both the nanoparticle and ssDNA in response to small quantities of complementary DNA. Specifically, the nick site 10 bases into the 20 bp duplex was programmed such that the melting temperature (Tm) of the nicked product would drop to approximately half that of the full 20 bp duplex (from ca. 60 to 30° C.). Through subsequent, thermodynamically favorable strand invasion, intact ssDNA or nanoparticle DNA is then allowed to hybridize to its complementary DNA in order to recycle the target.

Figure 2A:
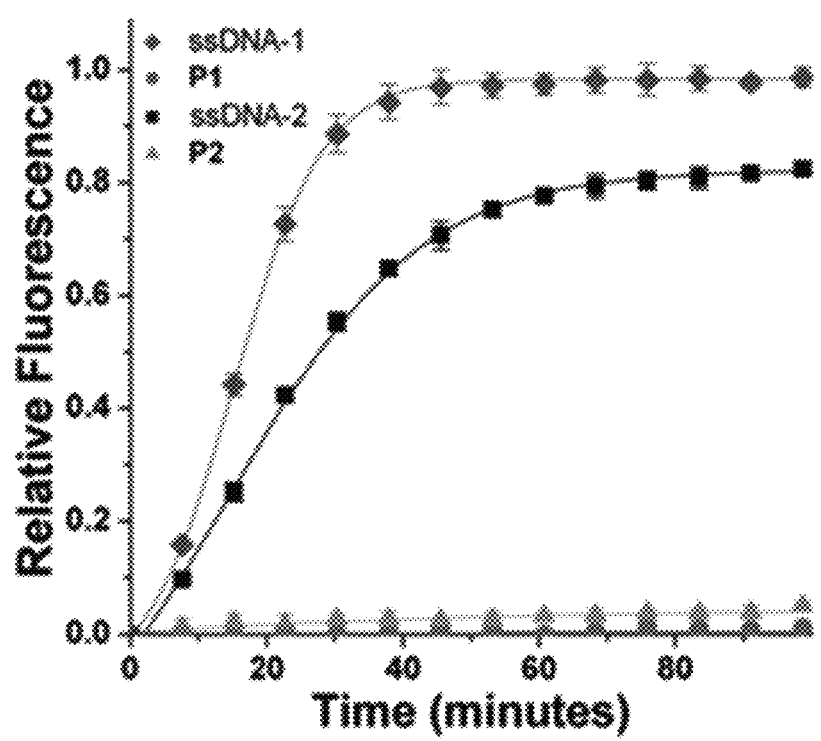
FIGS. 2A-2C. These figures depict endonuclease resistance of DPA nanoparticles.
Figure 2B:
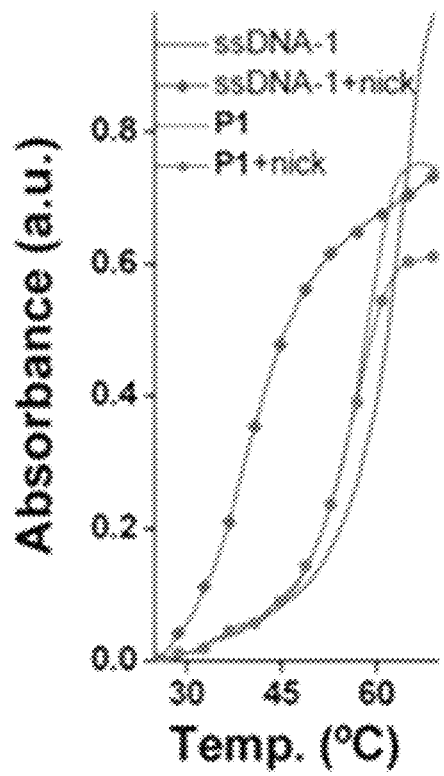
Figure 2C:
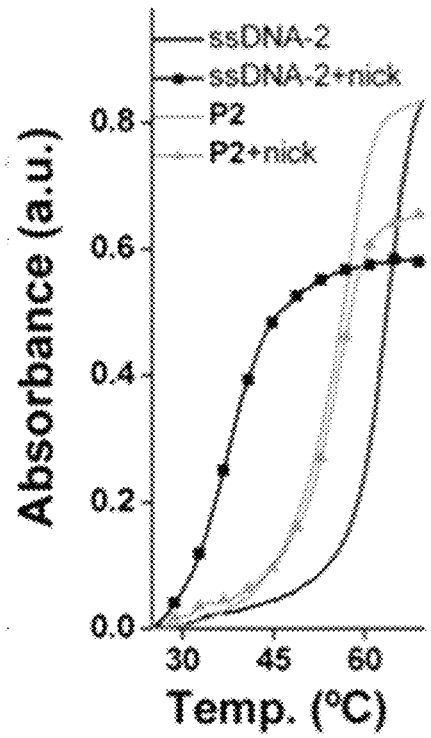

In order to monitor the activity of nicking endonuclease Nt.CviPII, two complementary analytical techniques were employed; namely, a fluorescence assay and an assessment of DNA melting temperature with and without enzyme treatment (FIGS. 2A-2C). The first method involves a fluorescence de-quenching experiment wherein the particles or ssDNA sequences, labeled with dye and quencher on either side of the nick site, are allowed to hybridize to complementary target DNA and are subsequently introduced to the endonuclease. Fluorescein fluorescence was monitored over time in order to assess the activity of the enzyme. In this case, an increase in fluorescein fluorescence corresponds to a nick in the dye-labeled sequence. Indeed, after hybridization to complementary DNA, the labeled ssDNA sequence is readily destroyed in the presence of the nicking endonuclease. On the contrary, the nanoparticles show virtually no activity via fluorescence, under identical conditions (FIG. 2A). Notably, this observation is independent of the arrangement of dye and quencher in the two types of substrate. Without wishing to be bound by any theory, it is believed that this is a critical observation, because for P1 there is the possibility that fluorescein may be quenched by neighboring, uncleaved strands within the particle shell, whereas this is not possible for P2, because the fluorescein should be free in solution following nicking. Alternatively, it was reasoned that perhaps the lack of fluorescence increase for both P1 and P2 could be due to the fact that a nicked sequence on the particle would not dissociate away due to the density of DNA in close proximity to the cleaved product. In order to rule out these possibilities, the Tm of both single-stranded and nanoparticle-based systems was analyzed following nuclease treatment (FIGS. 2B-2C). This analysis confirms that the activity of the endonuclease on the ssDNA-target duplex is accompanied by a significant decrease in the Tm of the duplex ($\Delta=-26.1°$ C. for ssDNA-1, $-26.1°$ C. for ssDNA-2), consistent with complete nicking of the oligonucleotide. By contrast, the Tm of the nanoparticle-target duplex remains consistent ($\Delta=-0.5°$ C. for P1, $-1.6°$ C. for P2) after nuclease treatment, thus indicating the presence of an intact 20-base oligonucleotide shell on the DPA nanoparticle.

Figure 3A:
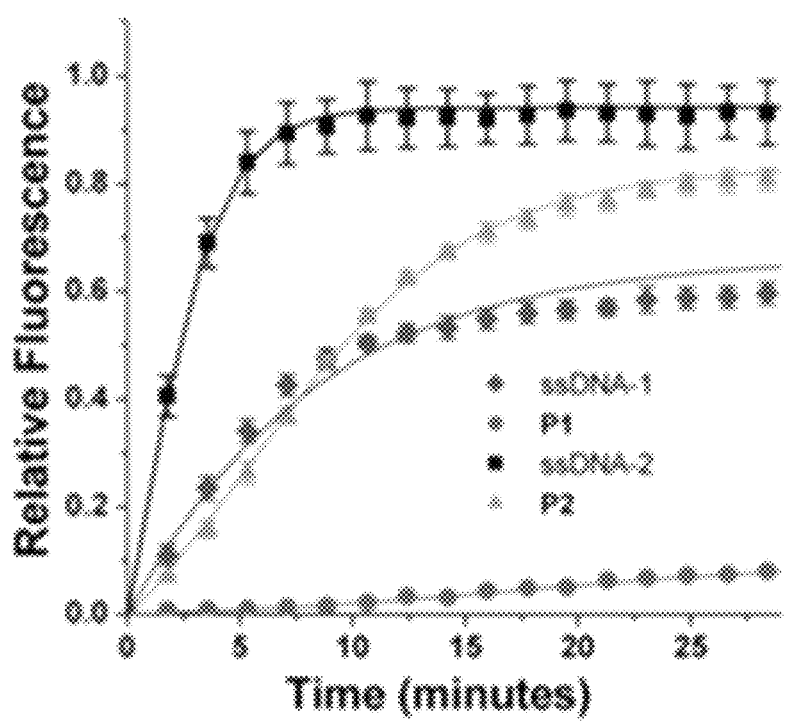
FIGS. 3A-3C. These figures depict exonuclease resistance of DPA nanoparticles.
Figure 3B:
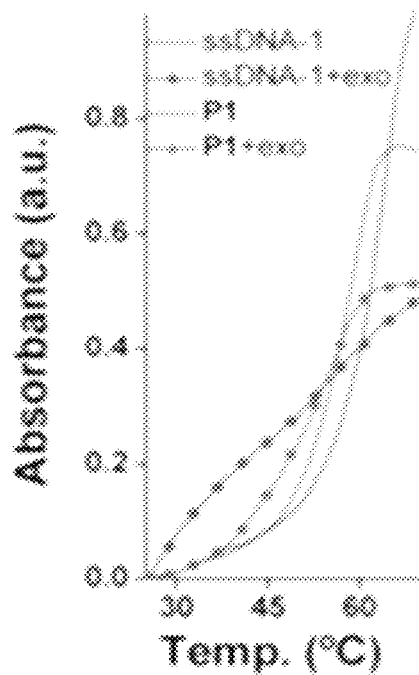
Figure 3C:
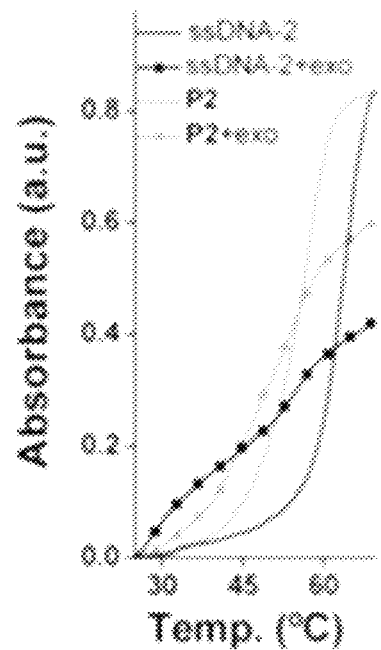

Given that DPA nanoparticles exhibit a high level of resistance against sequence specific nicking endonuclease Nt.CviPII, it was determined how DPA nanoparticles respond as substrates to a non-specific 3' exonuclease (FIGS. 3A-3C). For example, exonuclease III (ExoIII, from *E. coli*) is reported to catalyze the stepwise removal of mononucleotides from the 3'-hydroxyl termini of duplex DNA with preferred substrates being blunt or recessed 3' termini. See e.g., Putney, S. D., et all., 1981, *Proc. Natl Acad. Sci. USA* 78:7350-7354. However, it was determined in the current studies that the enzyme exhibits indiscriminate activity on both ssDNA and dsDNA substrates. Therefore, it was decided to analyze the activity of ExoIII against ssDNA and corresponding DPA-nanoparticles in the absence of any additional complementary DNA. ExoIII activity against ssDNA and DPA-nanoparticles was monitored via fluorescein fluorescence de-quenching over time. Initial observations implied that P1 was resistant, while P2 showed activity. A kinetic analysis of P2 with respect to ExoIII revealed that it is a significantly poorer substrate than ssDNA-2. See FIG. 3A and Table 1 following. See also FIGS. 12A-12G. It was reasoned that this apparent discrepancy between P1 and P2 could be due to the fact that for P2, the fluorescein-labeled nucleotide is located only one base from the 3' hydroxyl terminus. Therefore, liberation of the fluorescent product into solution (i.e., detection of fluorescence) only requires the removal of two bases. In the case of P1, the liberation of a DABCYL-labeled nucleotide does not have the same effect. Here, it was concluded that the fluorescein-labeled nucleotide is not liberated into solution but remains in an environment surrounded by DABCYL quencher molecules still present on unreacted, neighboring DNA strands as well as neighboring guanosine bases. See e.g., Nazarenko, I., et al., 2002, *Nucl. Acids Res.* 30:2089-2095. Therefore, P1 showing a different response to P2 when subjected to ExoIII, is consistent with the nuclease digesting a limited fraction of 3'-terminal bases.

TABLE 1

Exonuclease III kinetics on ssDNA-2 and P2 substrates.

| Substrate | Initial Rate ($\times 10^{-9}$ M/s) | Vmax ($\times 10^{-9}$ M/s) | Km ($\times 10^{6}$ M) | kcat $s^{-1}$ | kcat/Km ($\times 10^{5}$ M · s) |
|---|---|---|---|---|---|
| ssDNA-2 | 18.6 | 50 | 10.6 | 1.42 | 1.3 |
| P2 | 4.4 | 12.5 | 7.0 | 0.36 | 0.5 |

To confirm observations and conclusions drawn from fluorescence studies, and to determine the extent of digestion, a hybridization study via DNA duplex melting analyses was employed. DPA-nanoparticles or ssDNA analogues were allowed to react with ExoIII for 1 hour before deactivating the enzyme with EDTA and heat. Following enzyme deactivation, an equimolar quantity of complementary DNA was allowed to hybridize to the nanoparticle or ssDNA. Melting temperature analysis reveals the absence of a melting transition in the case of both ssDNA strands indicating complete degradation following enzyme treatment. See e.g., FIGS. 3B-3C. By contrast, in the case of enzyme-treated DPA-nanoparticles, P1 and P2, there was observed a sharp melting transition of the particle-duplex indicative of an intact DPA-nanoparticle. There was observed a slight decrease in the particle-duplex Tm (i.e., Δ=−3° C. in each case). This is consistent with fluorescence evidence suggesting that the enzyme digests several bases of the nanoparticle nucleic acid shell at the outer edge and is subsequently sterically hindered, thus preventing complete digestion. Indeed, the data are consistent with a duplex on the order of approximately 18 base pairs compared to 20 base pairs for the full-length sequence without enzymatic treatment. Therefore, it was concluded that the exonuclease is able to digest only a portion of the 3'-terminus, but leaves the particle-based nucleic acid largely intact. Indeed, encouraged by the results demonstrating DPA-nanoparticle resistance to ExoIII (FIG. 11), the particles were subjected to Snake Venom Phosphodiesterase (Phosphodiesterase I from *Crotalus adamanteus*) known for its high 3'-exonuclease activity and routinely utilized for complete digestion of oligonucleotides for sequence analysis. See e.g., Ho, N. W. Y. & Gilham, P. T., 1973, *Biochim. Biophysica Acta* 308: 53-58. Again, based on fluorescence dequenching analysis, the DPA-nanoparticles exhibit exceptional resistance consistent with observations made utilizing ExoIII.

Example 2. Studies on Cellular Mechanism of Action

Figure 14:
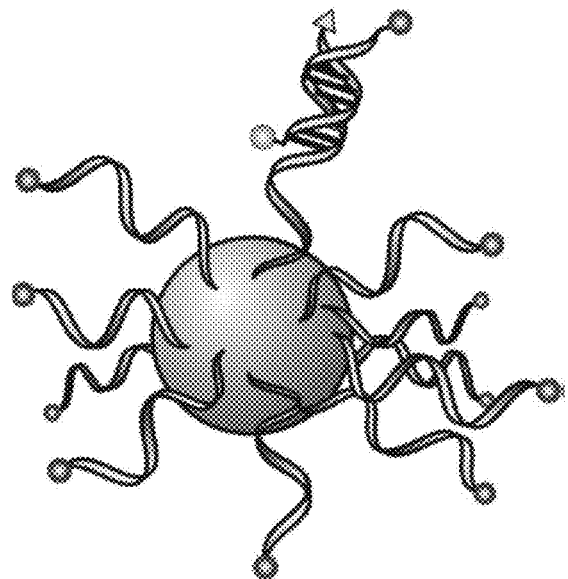
FIG. 14 is a cartoon showing a polymeric micelle as disclosed herein. The central sphere represents the aggregated polymer. The ribbon represents the nucleic acid strand that is covalently linked to the polymer, and the dot indicates a detectable label used for detection in experiments. The duplex bound ribbon is a nucleic acid at least partially complementary to the nucleic acid strand that is covalently linked to the polymer, which forms a heteroduplex therewith. It can be modified (e.g., at the 3' end or within the sequence) with a detectable label used for detection in experiments. It can be modified (e.g., at the 5' end) with a targeting ligand (triangle).

Nucleic acid, optionally including locked-nucleic acid, (DNA[LNA]) can be conjugated to a synthetic polymer, e.g., that has been synthesized by means of ring-opening metathesis polymerization (ROMP), as known in the art. In aqueous solution, this conjugate can spontaneously form polymeric micelles in an aqueous milieu. The nucleic acid sequences displayed at the exterior of the micelles can then be hybridized to a complementary DNA sequence (e.g., a 12 base sequence) that has been covalently modified with a ligand. In one embodiment, this ligand is (−)-2-β-Carbomethoxy-3-β-(4-fluorophenyl)tropane (β-CFT). The β-CFT ligand binds to the dopamine transporter (DAT), which is specific to a particular neuronal phenotype (the dopamine neuron). Through normal endocytic recycling of the DAT, the resulting complex can be endocytosed. The polymer and nucleic acid can be released into the cytoplasm by destabilizing of the membrane of the endosome through non-lamellar phase properties of the micelle, as known in the art. Once the nucleic acid is introduced into the cytoplasm, if its target is present, it can bind to and inhibit it through Watson-Crick base pairing. FIG. 14 provides a cartoon depiction of a micelle including a plurality of nucleic acid conjugates as disclosed herein.

Once inside the cell, the nucleic acid, if designed as a microRNA inhibitor, can inhibit the function of the microRNA of the cell by binding to it through Watson-Crick base-pairing. The modifications to the DNA[LNA] containing LNA that make it different from DNA are covalent cross-links across the phosphate backbone (O-methyl bridges), decreasing steric freedom and increasing the binding strength by orders of magnitude compared to unmodified nucleic acids. This action can permanently inhibit the cells' microRNA (of a specific sequence) from functioning. The details of representative nucleic acid sequences and base-pairing interactions are discussed following.

1. The nucleic acid is hybridized to the DNA[LNA] polymer, with overhang, as shown following:

DNA[LNA] Conjugated to Polymer

```
{polymer-5' (C6 amino)-TCATACAGCTAGATAACCAAAG-3'-(TAMRA)        (SEQ ID NO: 5)
                       ||||||||||||||
            Fluorescein-3'-dTCTATTGGTTTCTT-5'-amino-bCFT}       (SEQ ID NO: 6)
Ligand conjugated to DNA[LNA].
```

2. When the nucleic acid is introduced into the cytoplasm, the cell's microRNA can begin hybridizing to the overhang, and the heteroduplex can be disassembled leaving the nucleic acid hybridized to the cell's endogenous microRNA.

```
Locked nucleic acid conjugated to polymer
{polymer-5' (C6 amino)-TCATACAGCTAGATAACCAAAG-3'-(TAMRA) (SEQ ID NO: 5)
                       ||||||||||||||||||
                    3'-AGTATGTCTATTGGTTTC-5'}
MicroRNA inside cell                                     (SEQ ID NO: 7)
```

3. When the DNA[LNA]-DNA-polymer duplex is disassembled, the LNA-microRNA duplex is formed, rendering the microRNA non-functional. In this case, it was microRNA-9. The DNA conjugated to the ligand may be free to bond with DAT present in the cell, or destroyed by endogenous nucleases. The locked nucleic acids are protected by the O-methyl bridge from nuclease activity.

4. An exemplary construct follows.

```
DNA conjugated to ligand{ Fluorescein-
-amino-bCFT
                               (SEQ ID NO: 6)
   3'-dTCTATTGGTTTCTT-5'
```

The defining mechanisms of the process disclosed herein include the targeting ligand (here, β-CFT) allowing for cell-type specificity of delivery, and the polymeric micelle displaying the modified nucleic acid on the outside of the micelle.

Example 3. Toxicity Studies

It has been validated that compositions disclosed herein are not toxic compared with commercially available products, as described following.

Cell type: Primary human neurons were employed.

Treatment conditions: 4-hr or 24-hr, at 37° C., 5% $CO_2$.

Cell media: serum-free DMEM.

Reagents:

R1. Nucleic acid conjugate (SEQ ID NO:8). Underlines indicate LNA residues; "TAM" represents TAMRA:

R2. TAMRA-DNA[LNA] construct (SEQ ID NO: 28):

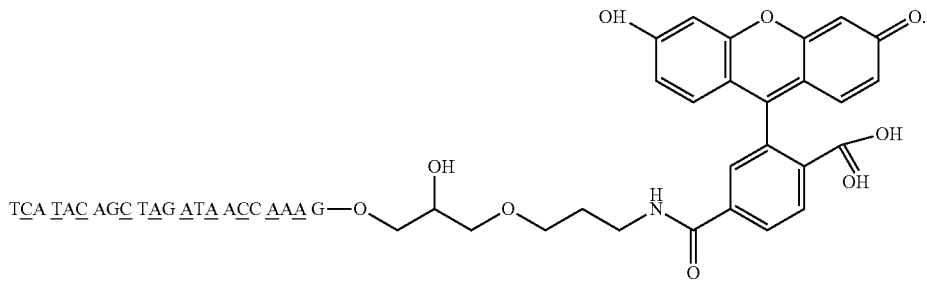

TCA TAC AGC TAG ATA ACC AAA G-3'-TAM.

R3. β-CFT-(C12 amino)-DNA-(3'-fluorescein). "Fl" is fluorescein:

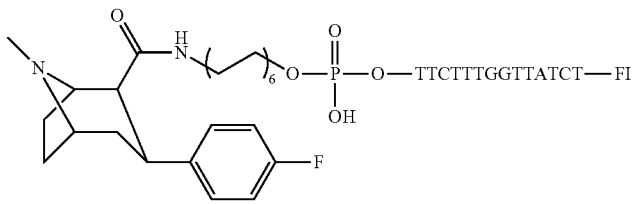

R4. Acetyl-DNA-(3'fluorescein): (SEQ ID NO: 9) Ac-TTCTTTGGTTATCT-Fl (SEQ ID NO: 10).

Figure 15:
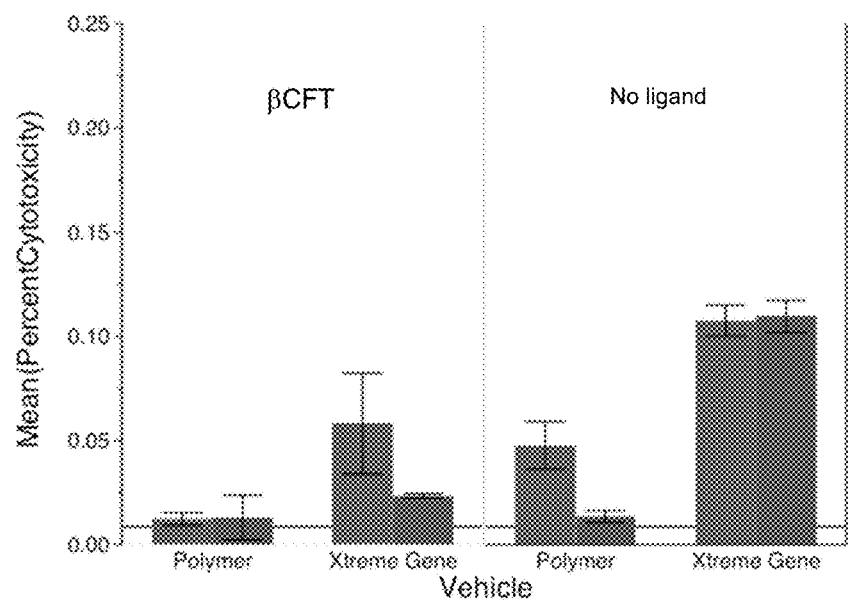
FIG. 15 is a histogram depicting cytotoxicity studies. Each pair of histogram bars represents 4-hr and 24-hr incubation with reagents, in order left to right, as disclosed in the Examples. Cytotoxicity is measured by lactic acid dehydrogenase (LDH) activity in the supernatant of primary human neurons. With intact cells, there is zero LDH activity in the supernatant, and complete cell lysis (induced by incubating with 1% Triton-X 100 for the indicated amount of time) is 100% cytotoxicity. Percent Cytotoxicity of the test compounds is determined by comparing LDH activity in the supernatant induced by the compound with that induced by 2% Triton-X 100. "β-CFT" refers to the presence of a cell specific targeting ligand (β-CFT) in the incubation reagent. "No ligand" refers to the absence of a cell specific targeting ligand in the incubation reagent. The line indicates standard error of the mean about zero, i.e., within detection limit of zero activity.

Incubation Conditions:

FIG. 15 (entry "Polymer" at far left): 50 pmol R1 plus 50 pmol R3, premixed in 10 mM $MgCl_2$ (100 uL volume) to allow hybridization, then mixed with 400 uL serum free DMEM (500 uL total volume). Time points for all pairs of data in histogram of FIG. 15 are in order (left to right), 4-hr and 24-hr.

FIG. 15 (entry "Xtreme Gene" second from left): 50 pmol R2 plus 50 pmol R3, mixed in presence of X-tremeGene siRNA Transfection Reagent (Roche). Reagents were diluted with serum free DMEM to a final volume of 500 uL.

FIG. 15 (entry "Polymer" third from left): 50 pmol R1 plus 50 pmol R4, premixed in 10 mM $MgCl_2$ (100 uL volume) to allow hybridization, then mixed with 400 uL serum free DMEM (500 uL total volume).

FIG. 15 (entry "Xtreme Gene" far right): 50 pmol R2 plus 50 pmol R4, mixed in presence of X-tremeGene siRNA Transfection Reagent (Roche). Reagents were diluted with serum free DMEM to a final volume of 500 uL.

Results.

As shown in FIG. 15, with intact cells, there is zero LDH activity in the supernatant, and complete cell lysis (induced by incubating with 1% Triton-X 100 for the indicated amount of time) is 100% cytotoxicity. Percent Cytotoxicity of the test compounds is determined by comparing LDH activity in the supernatant induced by the compound with that induced by 2% Triton-X 100. The line indicates standard error of the mean about zero, in other words, within detection limit of zero activity.

Example 4. Studies on Additional Cell Types

Astrocytes. A nucleic acid conjugate disclosed herein having a β-CFT cell specific targeting moiety were analyzed by confocal fluorescence microscopy in astrocytes, a phagocytic cell that does not express DAT. The punctate visualization of the fluorescein in confocal microscopy indicates that the compound is likely to be in endosomes, possibly through phagocytosis. Without wishing to be bound by any theory, it is believed that the disclosed nucleic acid conjugates may be non-functional in astrocytes.

SH-SY5Y cells. Nucleic acid conjugates disclosed herein having a β-CFT cell specific targeting moiety were analyzed by confocal fluorescence microscopy in SH-SY5Y cells, a DAT-expressing cell line. The nucleic acid conjugates are delivered into the cells and appears diffuse and cytoplasmic. In a control study wherein the nucleic acid conjugate lacked the β-CFT cell specific targeting moiety, the nanoparticles were observed to not enter the SH-SY5Y cells.

Mixed Neuronal Cultures. A nucleic acid conjugate disclosed herein having a β-CFT cell specific targeting moiety were analyzed by confocal fluorescence microscopy in mixed neuronal cultures. Results indicates that the conjugate is found in such cells that also express DAT.

HeLa cells and K562 cells. Uptake of a nucleic acid conjugate disclosed herein, having DNA sequence 5'-$C_{12}$amino-(TTT)$_3$-AA GGG CCT TTG AAC TCT GCT TT$_F$ (SEQ ID NO:11) and an overall structure as set forth in FIG. 1A, was examined in HeLa cells and K562 cells by fluorescence-activated cell sorting (FACS). In these studies, no cell specific targeting moiety was included. The subscript "F" (e.g., "$T_F$") refers to fluorescein labeling. The subscript "D" (e.g., "$T_D$") refers to DABCYL labeling.

Cells were treated with 5 nM micelle (i.e., approximately 1 micromolar DNA due to an assumed concentration of about 200 DNA molecules per nanoparticle) or with 1 uM ssDNA (fluorescein labeled), both in optimum reduced serum media for 4 hours. Then, media was removed and replaced with fresh OPTIMEM media prior to the cells being incubated overnight. The next day, the cells were washed twice with PBS and then trypsonized in order to facilitate lifting off from the multi-well plate surface. At this point the cells were collected, centrifuged and then resuspended in PBS. The cells were then subjected to analysis by FACS.

For both HeLa and K562 cells, much greater populations were observed for cells which have been treated with the DPA micelles, compared with cells treated with ssDNA. This indicated a much greater uptake of the DPA micelle as compared to the ssDNA. Without wishing to be bound by any theory, it is believed that nucleic acid uptake is greatly enhanced in the case of the micelles as compared to the ssDNA control due to the spherical, highly charged, higher molecular weight nature of the DNA polymer nanoparticles.

Example 5. Exemplary Roles for Nucleic Acid Conjugates

Exemplary uses for the nucleic acid conjugates disclosed herein include the following.

miRNA surrogates. Nucleic acid conjugates with structure set forth in FIG. 1A can be useful as miRNA surrogates or regulating agents in primary neurons. In one example, the nucleic acid can have sequence TTTCATACAGCTAGA-TAACCAAAG (SEQ ID NO:12), finding use, e.g., as an anti miR9 (SEQ ID NO:13) regulating agent.

Modulators of enzymatic activity. Nucleic acid conjugates with structure set forth in FIG. 1A can be useful as agents to limit or otherwise tailor enzymatic activity (e.g., nuclease digestion), particularly at surface-solution interfaces.

In one example, the nucleic acid can have sequence TTTAGAGT$_F$CATGTCCAGT CAGT$_D$G (SEQ ID NO:2), finding use, e.g., due to reduced Nt.CviPII activity, as disclosed herein. In one example, the nucleic acid can have sequence TTTAGAGT$_D$CATGTCCAGT CAGT$_F$G (SEQ ID NO:3), finding use, e.g., due to reduced Nt.CviPII activity, as disclosed herein. In one example, the nucleic acid can have sequence T$_D$ATCCAGTCAGT$_D$G (SEQ ID NO:14), finding use, e.g., due to reduced Nt.CviPII activity, as disclosed herein. In one example, the nucleic acid can have sequence (N)$_8$T$_F$CATGTCCAGTCA GT$_D$G (SEQ ID NO:15), finding use, e.g., due to reduced Nt.CviPII activity, as disclosed herein. In one example, the nucleic acid can have sequence (N)$_{38}$TFCATGTCCAGTCAGT$_D$G (SEQ ID NO:16), finding use, e.g., due to reduced Nt.CviPII activity, as disclosed herein.

In one example, the nucleic acid can have sequence TTTTTTTTAGAGT$_D$CATGAA GCTTCAGT$_F$G (SEQ ID NO:17), finding use, e.g., as a HindIII substrate. In one example, the nucleic acid can have sequence TTTTTTTT-TAGAGT$_D$CATGGGATCCCAGT$_F$G (SEQ ID NO:18), finding use, e.g., as a BamHI substrate. In one example, the nucleic acid can have sequence TTTTTTTTTAGAGT$_D$-CATGTCTAGACAGT$_F$G (SEQ ID NO:19), finding use, e.g., as an XbaI substrate.

Regulators of mRNA content. Nucleic acid conjugates with structure set forth in FIG. 1A can be useful as agents to study cell update of densely packed nucleic acid and regulate mRNA content intracellularly. In one example, the nucleic acid can have sequence TTTTTTTT-TAAGGGCTTTTGAACTCTGCTTT$_F$ (SEQ ID NO:20), finding use, e.g., as an anti BCR-ABL agent, as known in the art. In another example, the nucleic acid can have sequence AAAAAAAAACCCAGCCTTCCAGCTCCTTGAT$_F$ (SEQ ID NO:21), wherein the underlined residues indicate LNA bases, finding use, e.g., as an anti-survivin agent, as known in the art. In another example, the nucleic acid can have sequence AAAAAAAAAGTTCCATCC GTCTGCC CCCAATT$_F$ (SEQ ID NO:22), wherein the underlined residues indicate LNA bases, finding use, e.g., as a survivin scramble agent, as known in the art.

Example 6. Cell Specific Targeting Moieties

A representative synthesis scheme for β-CFT-labeled nucleic acid with spacer is set forth in Scheme 1 following, wherein "CPG" refers to controlled pore glass, and "Fl" refers to fluorescein.

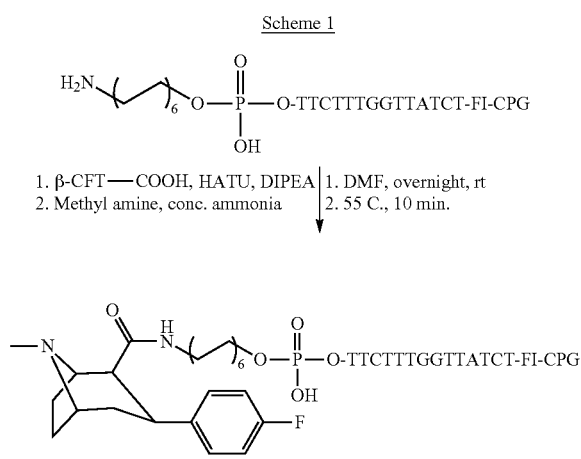

The nucleic acid sequence (SEQ ID NO:23), having a spacer at the 5'-terminal and a fluorescein moiety bound at the 3'terminal which is further bound to a controlled pore glass, is reacted with β-CFT-COOH under conditions suitable to afford the depicted β-CFI-labeled nucleic acid with spacer. MS: (m/z) 5551.17.

In another representative synthetic scheme, the spacer further includes a PEG$_{18}$ moiety. The term "PEG$_{18}$" in this context refers to a PEG moiety having 18 atoms. The synthesis is conducted under conditions suitable to afford the a β-CFI-labeled nucleic acid with spacer following (SEQ ID NO:24). MS: (m/z) 5894.82.

Example 7. Reagents Containing β-CFT

Synthesis of a β-CFT terminating agent can be conveniently conducted as disclosed, for example, in Scheme 2 following. The methyl ester can be converted to the acid by nucleophilic displacement in the presence of lithium n-propyl mercaptide and hexamethylphosphoramide linking reagent. See e.g., Bartlett, P. A. & Johnson, W. S., *Tetrahedron Letters* 1970, 11:4459-4462. The resulting acid moiety can be activated by NHS, and amide bond formation can occur with the methoxyeneamine to afford the target compound.

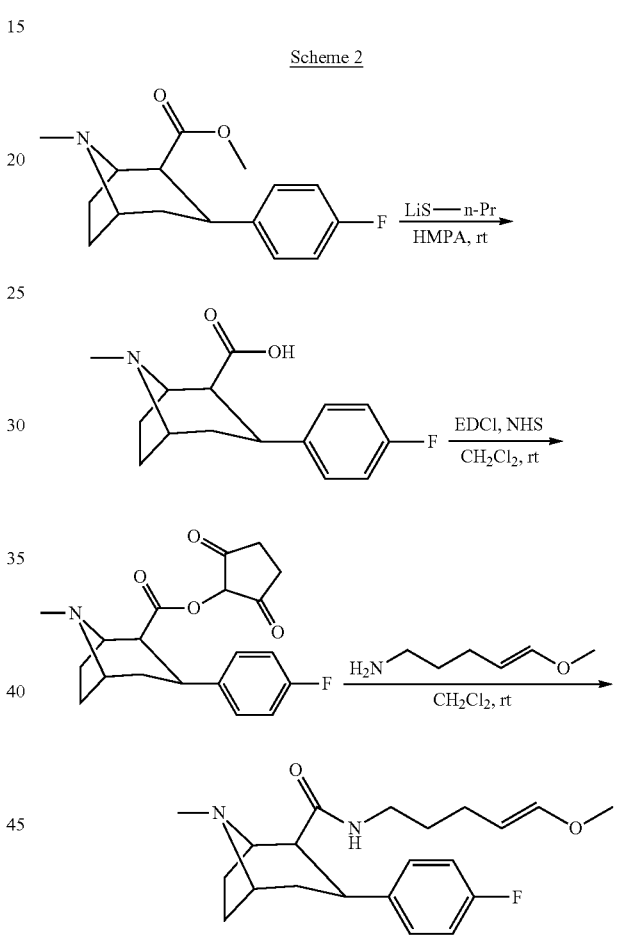

A monomer containing β-CFT can be conveniently synthesized, e.g., from the NHS adduct by amide bond formation with the norbornene amine having a desired spacer, as depicted in Scheme 3 following.

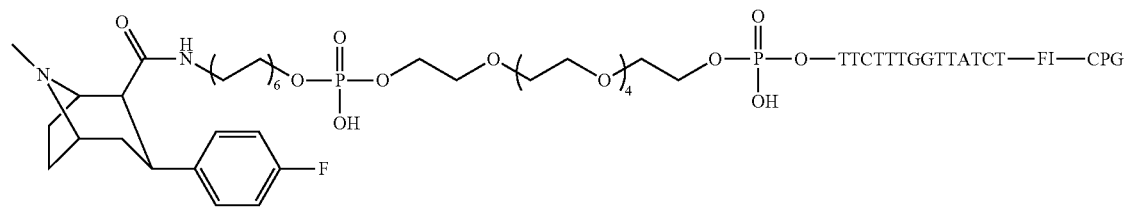

Scheme 3

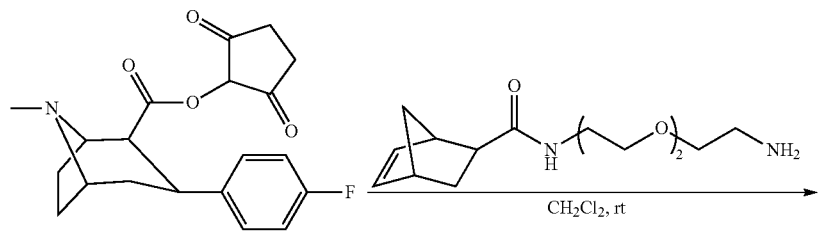

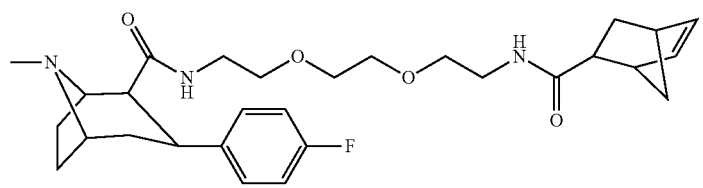

Incorporation of β-CFT can be conveniently achieved using phosphoramidite methods, e.g., in the solid-phase, as known in the art. A typical synthetic scheme is set forth in Scheme 4 following. Following Scheme 4, the substituted deoxynucleoside can be reacted with the aminoalkylacrylamide to form the adduct, the 3'-hydroxyl of which can be protected as the phosphoramidite prior to reaction with NHS-protected β-CFT to afford the reagent.

Scheme 4

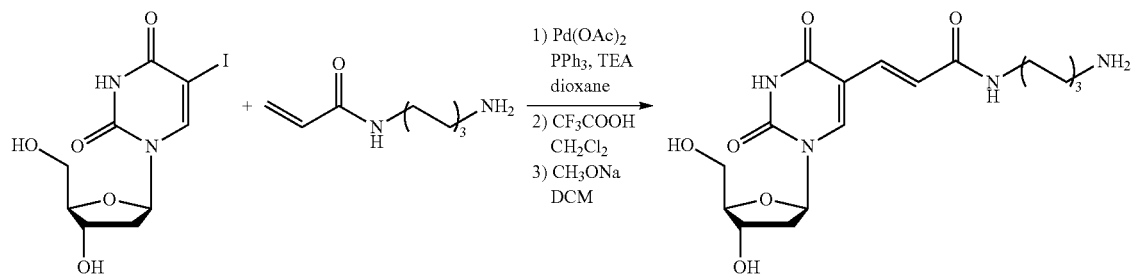

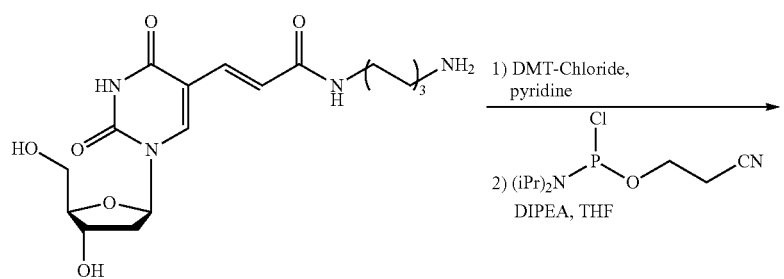

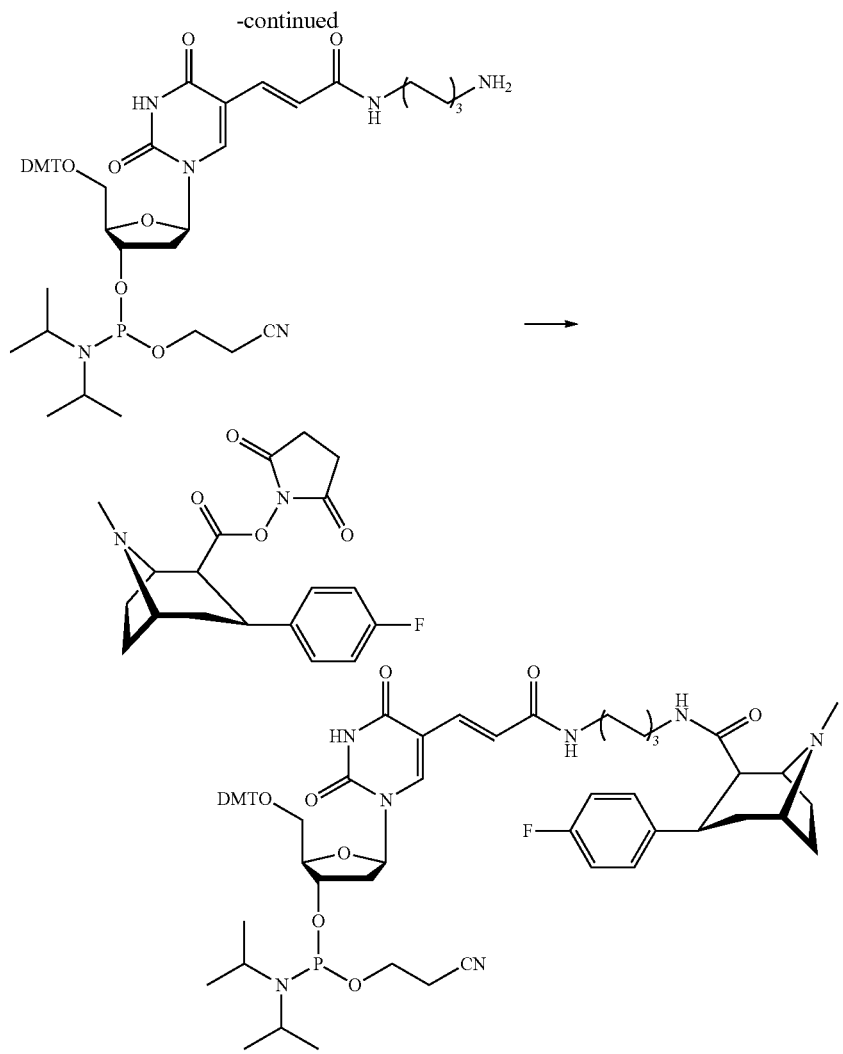

-continued

Example 8. Survivin mRNA Knockdown in HeLa Cells

In order to investigate cellular uptake in HeLa cells and subsequent activity, a nucleic acid conjugate was synthesized with structure S1 (FIG. 1A) having a C12 amino spacer and nucleic acid sequence TTTAAAAAA CCCAGCCTTCCAGCTCCTTGAT$_F$, wherein the underlined indicates LNA residues (SEQ ID NO:25).

Experimental Conditions

Day 0: plate HeLa cells at 20,000 cells per well in 24 well multi well plate (media: DMEM with 10% FBS).

Day 1: U (untreated)—remove media, treat with 300 ul Opti MEM® media; S (single micelle treatment)—remove media, treat with 300 ul 5 nM micelle in Opti MEM® media; D (daily micelle treatment)—remove media, treat with 5 nM micelle in Opti MEM® media. Incubate each condition for 4 hours, remove media, replace with 500 ul DMEM with 10% FBS.

Day 2: U, D—same as day 1. S—treat the same as for U.
Day 3: U, D, and S all treated same as day 2.
Day 4: U, D, and S all treated same as day 3.

Wash cells 2× with PBS, lyse cells with RLT buffer (RNeasy® Mini kit), treat with QIAshredder mini columns, transfer to RNeasy® spin columns. Follow RNeasy® protocol to extract cellular RNA. Digest DNA with Turbo™ DNase (Turbo DNA-free). Perform reverse transcription to make cDNA using Superscript™ III first strand synthesis system and following Superscript™ III protocol using oligo dT primers.

Perform qPCR using Fast SYBR® green master mix. Survivin forward primer: 5'-ATG GGT GCC CCG ACG TTG-3' (SEQ ID NO:26), survivin reverse primer: 5'-AGA GGC CTC AAT CCA TGG-3' (SEQ ID NO:27). qPCR was normalized to endogenous GapDH.

Results

Figure 16:
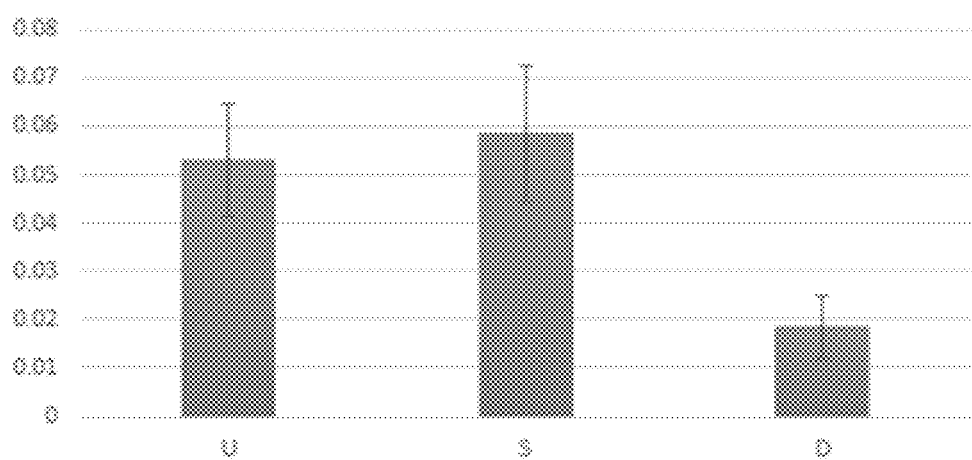
FIG. 16 is a histogram depicting results of RT qPCR analysis of survivin mRNA in HeLa cells. Legend (left to right): U (untreated); S (single treatment); D (daily treatment). Treatment was with nucleic acid conjugate as described in the Example. Y-axis: Gene expression expressed as $2^{(Ct[Survivin]-Ct[GapDH])}$, where Ct[Survivin] and Ct[GapDH] are the points in the PCR cycle at which the fluorescent threshold is reached for survivin and GapDH, respectively.

The histogram of FIG. 16 provides the results for the U, S and D cases described above. The Y-axis of the histogram is gene expression expressed as $2^{-(Ct[Survivin]-Ct[GapDH])}$, where Ct[Survivin] and Ct[GapDH] are the points in the PCR cycle at which the fluorescent threshold is reached for survivin and GapDH, respectively, as known in the art. As depicted in the histogram of FIG. 16, daily treatment with the nucleic acid conjugate resulted in significant decrease in survivin mRNA in HeLa cells over the time course of the experiment, compared with untreated and single treatment protocols.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference and for all purposes.

The foregoing description is illustrative of particular embodiments of the invention, but is not meant to be a limitation upon the practice thereof. The following claims, including all equivalents thereof, are intended to define the scope of the invention.

XI. Embodiments

Embodiment 1

A nucleic acid conjugate including: a first oligonucleotide including up to about 200 bases, wherein the first oligonucleotide is complementary to a target sequence associated with aberrant physiological activity, and a hydrophobic polymer covalently bound to the first oligonucleotide through a first linker; wherein the conjugate forms nanoparticulate micelles having a hydrophobic core and a hydrophilic shell; wherein the hydrophobic core includes a plurality of hydrophobic polymer moieties; and wherein the hydrophilic shell includes a high density of the first oligonucleotide.

Embodiment 2

The conjugate of embodiment 1, wherein the first oligonucleotide is a DNA, an RNA or a locked nucleic acid (LNA).

Embodiment 3

The conjugate of embodiment 1, wherein the hydrophobic polymer is a hydrophobic block copolymer or hydrophobic homopolymer.

Embodiment 4

The conjugate of embodiment 1, wherein the hydrophobic polymer is selected from polymers made by catalytic chain transfer, iniferter mediated polymerization, stable free radical mediated polymerization (SFRP), atom transfer radical polymerization (ATRP), reversible addition fragmentation chain transfer polymerization (RAFT), iodine-transfer polymerization, or ring opening metathesis polymerization.

Embodiment 5

The conjugate of embodiment 4, wherein the hydrophobic polymer is prepared by ring opening metathesis polymerization.

Embodiment 6

The conjugate of embodiment 1, wherein the hydrophobic polymer is covalently linked, directly or indirectly, to the first oligonucleotide via an amide bond.

Embodiment 7

The conjugate of embodiment 1, wherein the high density of the first oligonucleotide includes at least 20 oligonucleotides per micellar nanoparticle.

Embodiment 8

The conjugate of embodiment 1, further including a first cell specific targeting moiety covalently linked to the first linker.

Embodiment 9

The conjugate of embodiment 1, further including a first cell specific targeting moiety covalently bound to the first oligonucleotide, optionally through a second linker.

Embodiment 10

The conjugate of embodiment 9, further including a second cell specific targeting moiety covalently bound to the hydrophobic polymer, optionally through a third linker.

Embodiment 11

The conjugate of embodiment 1, further including a first cell specific targeting moiety covalently bound to the hydrophobic polymer, optionally through a fourth linker.

Embodiment 12

The conjugate of embodiment 1, further including a second oligonucleotide which is at least partially complementary to the first oligonucleotide.

Embodiment 13

The conjugate of embodiment 12, wherein the second oligonucleotide is hybridized to the first oligonucleotide.

Embodiment 14

The conjugate of any one of embodiments 12 to 13, further including a detectable label.

Embodiment 15

The conjugate of any one of embodiments 12 or 13, wherein the second oligonucleotide further includes a first cell specific targeting moiety covalently bound thereto, optionally through a fifth linker.

Embodiment 16

The conjugate of embodiment 15, further comprising a detectable label.

Embodiment 17

A targeted polymer nanoparticle comprising a plurality of nucleic acid conjugates according to any one of embodiments 8, 9, 10, or 11.

Embodiment 18

A targeted polymer nanoparticle comprising a plurality of nucleic acid conjugates according to embodiment 15.

Embodiment 19

A micelle comprising a plurality of nucleic acid conjugates according to any one of embodiments 1 to 13.

Embodiment 20

The micelle of embodiment 19, the micelle having a second oligonucleotide which is at least partially complementary to the first oligonucleotide, wherein the second oligonucleotide comprises a first cell specific targeting moiety covalently attached thereto.

Embodiment 21

The micelle of embodiment 20, wherein the second oligonucleotide comprises a detectable label covalently attached thereto.

Embodiment 22

A formulation comprising the conjugate of any one of embodiments 1 to 13 in a pharmaceutically acceptable carrier therefore.

Embodiment 23

A formulation comprising the conjugate of embodiment 15 in a pharmaceutically acceptable carrier therefore.

Embodiment 24

A method of making a nucleic acid conjugate according to embodiment 1, the method comprising reacting a first oligonucleotide comprising up to about 200 bases with a carboxylic acid terminated, hydrophobic polymer, optionally in the further presence of a first linker.

Embodiment 25

A method for delivery of an oligonucleotide into a target cell, the method comprising administering an effective amount of a formulation according to embodiment 22 to a subject in need thereof.

Embodiment 26

A method to impart endonuclease resistance to a first oligonucleotide, wherein the first oligonucleotide has a defined sequence, the method comprising incorporating the first oligonucleotide into a conjugate according to embodiment 1, and forming a micelle therefrom prior to exposure of the first oligonucleotide to an endonuclease.

---

What is claimed is:

1. A micelle comprising a plurality of nucleic acid conjugates, each of said nucleic acid conjugates comprising:
   a first oligonucleotide comprising up to about 200 bases, wherein said first oligonucleotide is complementary to a target sequence associated with aberrant physiological activity, and
   a cyclic olefin polymer covalently bound to said first oligonucleotide through a first linker, wherein said first linker comprises an alkylene of at least 12 carbons;
   wherein each of said conjugates forms nanoparticulate micelles having a hydrophobic core and a hydrophilic shell;
   wherein said hydrophobic core comprises a plurality of cyclic olefin polymer moieties; and
   wherein said hydrophilic shell comprises a high density of said first oligonucleotide.

2. The micelle of claim 1, wherein said first oligonucleotide is a DNA, an RNA or a locked nucleic acid (LNA).

3. The micelle of claim 1, wherein said cyclic olefin polymer is covalently linked, directly or indirectly, to said first oligonucleotide via an amide bond.

4. The micelle of claim 1, wherein said high density of said first oligonucleotide comprises at least 20 oligonucleotides per micellar nanoparticle.

5. The micelle of claim 1, further comprising a second oligonucleotide which is at least partially complementary to said first oligonucleotide.

6. A formulation comprising the micelle of claim 1 in a pharmaceutically acceptable carrier therefore.

7. A method for delivery of a micelle into a target cell, said method comprising administering an effective amount of a formulation according to claim 6 to a subject in need thereof.

8. A method to impart endonuclease resistance to a micelle comprising a plurality of nucleic acid conjugates of claim 1, said method comprising incorporating said nucleic acid conjugates into a micelle according to claim 1 prior to exposure of said micelle to an endonuclease, thereby imparting endonuclease resistance to said micelle comprising a plurality of nucleic acid conjugates.

* * * * *

UNITED STATES PATENT AND TRADEMARK OFFICE
CERTIFICATE OF CORRECTION

PATENT NO. : 10,046,057 B2  
APPLICATION NO. : 14/667283  
DATED : August 14, 2018  
INVENTOR(S) : Erick T. Tatro et al.

Page 1 of 1

It is certified that error appears in the above-identified patent and that said Letters Patent is hereby corrected as shown below:

In the Specification

STATEMENT AS TO RIGHTS TO INVENTIONS MADE UNDER FEDERALLY SPONSORED RESEARCH AND DEVELOPMENT section, Column 1, Lines 20-23, delete:
"This invention was made with Government support under grant numbers 1R03DA031591 and OD008724, awarded by the National Institutes of Health. The Government has certain rights in this invention."

And insert:
--This invention was made with government support under DA031591 and OD008724 awarded by the National Institutes of Health. The government has certain rights in the invention.--

Signed and Sealed this  
Tenth Day of February, 2026

John A. Squires  
*Director of the United States Patent and Trademark Office*

SEQUENCE LISTING

```
<160> NUMBER OF SEQ ID NOS: 28

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1
tttagagtca tgtccagtca gtg                                              23

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: Residue modified with fluorescein
<220> FEATURE:
<221> NAME/KEY: misc_feature
<222> LOCATION: (22)..(22)
<223> OTHER INFORMATION: Residue modified with DABCYL

<400> SEQUENCE: 2
tttagagtca tgtccagtca gtg                                              23

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: Residue moidifed with DABCYL
```

```
<220> FEATURE:
<221> NAME/KEY: misc_feature
<222> LOCATION: (22)..(22)
<223> OTHER INFORMATION: Residue moidifed with fluorescein

<400> SEQUENCE: 3
tttagagtca tgtccagtca gtg                                              23

<210> SEQ ID NO 4
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 4
tattatatct ttagacactg actggacatg actct                                 35

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Residue modified at 5'-terminal with spacer in
      turn modified with  polymer
<220> FEATURE:
<221> NAME/KEY: misc_feature
<222> LOCATION: (2)..(22)
<223> OTHER INFORMATION: Residue moidified at 3'-terminal with TAMRA

<400> SEQUENCE: 5
tcatacagct agataaccaa ag                                               22

<210> SEQ ID NO 6
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Resdiue modified at 5'-terminal with bCFT
<220> FEATURE:
<221> NAME/KEY: misc_feature
<222> LOCATION: (14)..(14)
<223> OTHER INFORMATION: Resdiue modified at 3'-terminal with
      fluorescein

<400> SEQUENCE: 6
ttctttggtt atct                                                        14

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 7
ctttggttat ctgtatga                                                    18
```

```
<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Residue at 5'-terminal modified with spacer in
      turn modified with polymer
<220> FEATURE:
<221> NAME/KEY: misc_feature
<222> LOCATION: (2)..(2)
<223> OTHER INFORMATION: Residue is locked nucleic acid at ribosyl ring
<220> FEATURE:
<221> NAME/KEY: misc_feature
<222> LOCATION: (4)..(4)
<223> OTHER INFORMATION: Residue is locked nucleic acid at ribosyl ring
<220> FEATURE:
<221> NAME/KEY: misc_feature
<222> LOCATION: (6)..(6)
<223> OTHER INFORMATION: Residue is locked nucleic acid at ribosyl ring
<220> FEATURE:
<221> NAME/KEY: misc_feature
<222> LOCATION: (9)..(9)
<223> OTHER INFORMATION: Residue is locked nucleic acid at ribosyl ring
<220> FEATURE:
<221> NAME/KEY: misc_feature
<222> LOCATION: (11)..(11)
<223> OTHER INFORMATION: Residue is locked nucleic acid at ribosyl ring
<220> FEATURE:
<221> NAME/KEY: misc_feature
<222> LOCATION: (13)..(13)
<223> OTHER INFORMATION: Residue is locked nucleic acid at ribosyl ring
<220> FEATURE:
<221> NAME/KEY: misc_feature
<222> LOCATION: (15)..(15)
<223> OTHER INFORMATION: Residue is locked nucleic acid at ribosyl ring
<220> FEATURE:
<221> NAME/KEY: misc_feature
<222> LOCATION: (17)..(17)
<223> OTHER INFORMATION: Residue is locked nucleic acid at ribosyl ring
<220> FEATURE:
<221> NAME/KEY: misc_feature
<222> LOCATION: (19)..(19)
<223> OTHER INFORMATION: Residue is locked nucleic acid at ribosyl ring
<220> FEATURE:
<221> NAME/KEY: misc_feature
<222> LOCATION: (21)..(21)
<223> OTHER INFORMATION: Residue is locked nucleic acid at ribosyl ring

<400> SEQUENCE: 8
tcatacagct agataaccaa ag                                              22

<210> SEQ ID NO 9
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Resdiue at 5'-terminal modified with spacer in
      turn modified the bCFT
<220> FEATURE:
<221> NAME/KEY: misc_feature
<222> LOCATION: (14)..(14)
<223> OTHER INFORMATION: Resdiue at 3'-terminal modified with
      fluorescein

<400> SEQUENCE: 9
ttctttggtt atct                                                       14
```

```
<210> SEQ ID NO 10
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Residue at 5'-terminal is acetylated
<220> FEATURE:
<221> NAME/KEY: misc_feature
<222> LOCATION: (14)..(14)
<223> OTHER INFORMATION: Residue at 3'-terminal is modified with
      fluorescein

<400> SEQUENCE: 10
ttctttggtt atct                                                       14

<210> SEQ ID NO 11
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: Residue at 3'-terminal is modified with
      fluorescein

<400> SEQUENCE: 11 tttttttta agggcctttg aactctgctt t                                     31

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
tttcatacag ctagataacc aaag                                            24

<210> SEQ ID NO 13
<211> LENGTH: 89
<212> TYPE: DNA
<213> ORGANISM: Homo sapiens

<400> SEQUENCE: 13
cggggttggt tgttatcttt ggttatctag ctgtatgagt ggtgtggagt cttcataaag     60
ctagataacc gaaagtaaaa ataacccca                                       89

<210> SEQ ID NO 14
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Residue at 5'-terminal is modified with DABCYL
<220> FEATURE:
<221> NAME/KEY: misc_feature
<222> LOCATION: (12)..(12)
<223> OTHER INFORMATION: Residue is modified with DABCYL
```

<400> SEQUENCE: 14
tatccagtca gtg                                                              13

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (9)..(9)
<223> OTHER INFORMATION: Residue modified with fluorescein
<220> FEATURE:
<221> NAME/KEY: misc_feature
<222> LOCATION: (23)..(23)
<223> OTHER INFORMATION: Residue modified with DABCYL

<400> SEQUENCE: 15
nnnnnnnntc atgtccagtc agtg                                                  24

<210> SEQ ID NO 16
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(38)
<223> OTHER INFORMATION: n is a, c, g, or t
<220> FEATURE:
<221> NAME/KEY: misc_feature
<222> LOCATION: (39)..(39)
<223> OTHER INFORMATION: Residue is modified with fluorescein
<220> FEATURE:
<221> NAME/KEY: misc_feature
<222> LOCATION: (53)..(53)
<223> OTHER INFORMATION: Residue is modified with DABCYL

<400> SEQUENCE: 16
nnnnnnnnnn nnnnnnnnnn nnnnnnnnnn nnnnnnnntc atgtccagtc agtg                 54

<210> SEQ ID NO 17
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (14)..(14)
<223> OTHER INFORMATION: Residue is modified with DABCYL
<220> FEATURE:
<221> NAME/KEY: misc_feature
<222> LOCATION: (28)..(28)
<223> OTHER INFORMATION: Residue is modified with fluorescein

<400> SEQUENCE: 17 tttttttta gagtcatgaa gcttcagtg                                              29

<210> SEQ ID NO 18
<211> LENGTH: 29
<212> TYPE: DNA
<213> ORGANISM: Artificial Sequence
<220> FEATURE:
<223> OTHER INFORMATION: Synthetic oligonucleotide

```
<220> FEATURE:
<221> NAME/KEY: misc_feature
<222> LOCATION: (14)..(14)
<223> OTHER INFORMATION: Residue is modified with DABCYL
<220> FEATURE:
<221> NAME/KEY: misc_feature
<222> LOCATION: (28)..(28)
<223> OTHER INFORMATION: Residue is modified with fluorescein

<400> SEQUENCE: 18 tttttttta gagtcatggg atcccagtg                                      29

<210> SEQ ID NO 19
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (14)..(14)
<223> OTHER INFORMATION: Residue is modified with DABCYL
<220> FEATURE:
<221> NAME/KEY: misc_feature
<222> LOCATION: (28)..(28)
<223> OTHER INFORMATION: Residue is modified with fluorescein

<400> SEQUENCE: 19 tttttttta gagtcatgtc tagacagtg                                      29

<210> SEQ ID NO 20
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: Residue is modified with fluorescein

<400> SEQUENCE: 20 tttttttta agggcttttg aactctgctt t                                   31

<210> SEQ ID NO 21
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Residue is locked nucleic acid at ribosyl ring
<220> FEATURE:
<221> NAME/KEY: misc_feature
<222> LOCATION: (11)..(11)
<223> OTHER INFORMATION: Residue is locked nucleic acid at ribosyl ring
<220> FEATURE:
<221> NAME/KEY: misc_feature
<222> LOCATION: (12)..(12)
<223> OTHER INFORMATION: Residue is locked nucleic acid at ribosyl ring
<220> FEATURE:
<221> NAME/KEY: misc_feature
<222> LOCATION: (13)..(13)
<223> OTHER INFORMATION: Residue is locked nucleic acid at ribosyl ring
<220> FEATURE:
<221> NAME/KEY: misc_feature
<222> LOCATION: (26)..(26)
<223> OTHER INFORMATION: Residue is locked nucleic acid at ribosyl ring
```

```
<220> FEATURE:
<221> NAME/KEY: misc_feature
<222> LOCATION: (27)..(27)
<223> OTHER INFORMATION: Residue is locked nucleic acid at ribosyl ring
<220> FEATURE:
<221> NAME/KEY: misc_feature
<222> LOCATION: (28)..(28)
<223> OTHER INFORMATION: Residue is locked nucleic acid at ribosyl ring
<220> FEATURE:
<221> NAME/KEY: misc_feature
<222> LOCATION: (29)..(29)
<223> OTHER INFORMATION: Residue is locked nucleic acid at ribosyl ring
<220> FEATURE:
<221> NAME/KEY: misc_feature
<222> LOCATION: (31)..(31)
<223> OTHER INFORMATION: Residue at 3'-terminal is modified with
      fluorescein

<400> SEQUENCE: 21
aaaaaaaaac ccagccttcc agctccttga t                                      31

<210> SEQ ID NO 22
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Residue is locked nucleic acid at ribosyl ring
<220> FEATURE:
<221> NAME/KEY: misc_feature
<222> LOCATION: (11)..(11)
<223> OTHER INFORMATION: Residue is locked nucleic acid at ribosyl ring
<220> FEATURE:
<221> NAME/KEY: misc_feature
<222> LOCATION: (12)..(12)
<223> OTHER INFORMATION: Residue is locked nucleic acid at ribosyl ring
<220> FEATURE:
<221> NAME/KEY: misc_feature
<222> LOCATION: (13)..(13)
<223> OTHER INFORMATION: Residue is locked nucleic acid at ribosyl ring
<220> FEATURE:
<221> NAME/KEY: misc_feature
<222> LOCATION: (26)..(26)
<223> OTHER INFORMATION: Residue is locked nucleic acid at ribosyl ring
<220> FEATURE:
<221> NAME/KEY: misc_feature
<222> LOCATION: (27)..(27)
<223> OTHER INFORMATION: Residue is locked nucleic acid at ribosyl ring
<220> FEATURE:
<221> NAME/KEY: misc_feature
<222> LOCATION: (28)..(28)
<223> OTHER INFORMATION: Residue is locked nucleic acid at ribosyl ring
<220> FEATURE:
<221> NAME/KEY: misc_feature
<222> LOCATION: (29)..(29)
<223> OTHER INFORMATION: Residue is locked nucleic acid at ribosyl ring
<220> FEATURE:
<221> NAME/KEY: misc_feature
<222> LOCATION: (32)..(32)
<223> OTHER INFORMATION: Residue at 3'=terminal is modified with
      fluorescein

<400> SEQUENCE: 22
aaaaaaaaag ttccatccgt ctgcccccaa tt                                     32

<210> SEQ ID NO 23
<211> LENGTH: 14
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (1)..(1)
<223> OTHER INFORMATION: Resdiue at 5'-terminal modified with spacer in
      turn modified with bCFT
<220> FEATURE:
<221> NAME/KEY: misc_feature
<222> LOCATION: (14)..(14)
<223> OTHER INFORMATION: Resdiue at 3'-terminal modified with
      fluorescein

<400> SEQUENCE: 23
ttctttggtt atct                                                      14

<210> SEQ ID NO 24
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Residue at 5'-terminal modified with PEG spacer
      in turn modified with bCFT.
<220> FEATURE:
<221> NAME/KEY: misc_feature
<222> LOCATION: (14)..(14)
<223> OTHER INFORMATION: Residue at 3'-terminal modified fluorescein

<400> SEQUENCE: 24
ttctttggtt atct                                                      14

<210> SEQ ID NO 25
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Residue is locked nucleic acid at ribosyl ring
<220> FEATURE:
<221> NAME/KEY: misc_feature
<222> LOCATION: (11)..(11)
<223> OTHER INFORMATION: Residue is locked nucleic acid at ribosyl ring
<220> FEATURE:
<221> NAME/KEY: misc_feature
<222> LOCATION: (12)..(12)
<223> OTHER INFORMATION: Residue is locked nucleic acid at ribosyl ring
<220> FEATURE:
<221> NAME/KEY: misc_feature
<222> LOCATION: (13)..(13)
<223> OTHER INFORMATION: Residue is locked nucleic acid at ribosyl ring
<220> FEATURE:
<221> NAME/KEY: misc_feature
<222> LOCATION: (26)..(26)
<223> OTHER INFORMATION: Residue is locked nucleic acid at ribosyl ring
<220> FEATURE:
<221> NAME/KEY: misc_feature
<222> LOCATION: (27)..(27)
<223> OTHER INFORMATION: Residue is locked nucleic acid at ribosyl ring
<220> FEATURE:
<221> NAME/KEY: misc_feature
<222> LOCATION: (28)..(28)
<223> OTHER INFORMATION: Residue is locked nucleic acid at ribosyl ring
<220> FEATURE:
<221> NAME/KEY: misc_feature
<222> LOCATION: (29)..(29)
<223> OTHER INFORMATION: Residue is locked nucleic acid at ribosyl ring
```

```
<220> FEATURE:
<221> NAME/KEY: misc_feature
<222> LOCATION: (31)..(31)
<223> OTHER INFORMATION: Residue at 3'-terminal is modified with
      fluorescein

<400> SEQUENCE: 25
tttaaaaaac ccagccttcc agctccttga t                                        31

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 26
atgggtgccc cgacgttg                                                       18

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 27
agaggcctca atccatgg                                                       18

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: Residue is locked nucleic acid at ribosyl ring
<220> FEATURE:
<221> NAME/KEY: misc_feature
<222> LOCATION: (4)..(4)
<223> OTHER INFORMATION: Residue is locked nucleic acid at ribosyl ring
<220> FEATURE:
<221> NAME/KEY: misc_feature
<222> LOCATION: (6)..(6)
<223> OTHER INFORMATION: Residue is locked nucleic acid at ribosyl ring
<220> FEATURE:
<221> NAME/KEY: misc_feature
<222> LOCATION: (9)..(9)
<223> OTHER INFORMATION: Residue is locked nucleic acid at ribosyl ring
<220> FEATURE:
<221> NAME/KEY: misc_feature
<222> LOCATION: (11)..(11)
<223> OTHER INFORMATION: Residue is locked nucleic acid at ribosyl ring
<220> FEATURE:
<221> NAME/KEY: misc_feature
<222> LOCATION: (13)..(13)
<223> OTHER INFORMATION: Residue is locked nucleic acid at ribosyl ring
<220> FEATURE:
<221> NAME/KEY: misc_feature
<222> LOCATION: (15)..(15)
<223> OTHER INFORMATION: Residue is locked nucleic acid at ribosyl ring
<220> FEATURE:
<221> NAME/KEY: misc_feature
<222> LOCATION: (17)..(17)
<223> OTHER INFORMATION: Residue is locked nucleic acid at ribosyl ring
<220> FEATURE:
<221> NAME/KEY: misc_feature
<222> LOCATION: (19)..(19)
<223> OTHER INFORMATION: Residue is locked nucleic acid at ribosyl ring
```

```
<220> FEATURE:
<221> NAME/KEY: misc_feature
<222> LOCATION: (21)..(21)
<223> OTHER INFORMATION: Residue is locked nucleic acid at ribosyl ring
<220> FEATURE:
<221> NAME/KEY: misc_feature
<222> LOCATION: (22)..(22)
<223> OTHER INFORMATION: Residue iat 3-'terminal modified with spacer in
      turn modified with TAMRA

<400> SEQUENCE: 28
tcatacagct agataaccaa ag                                             22
```